US011021521B2

(12) United States Patent
Zgurskaya et al.

(10) Patent No.: US 11,021,521 B2
(45) Date of Patent: Jun. 1, 2021

(54) PORE-MODIFIED GRAM-NEGATIVE BACTERIA AND USES THEREOF

(71) Applicant: The Board of Regents of the University of Oklahoma, Norman, OK (US)

(72) Inventors: Helen Zgurskaya, Norman, OK (US); Jon W. Weeks, Laurel, MD (US)

(73) Assignee: THE BOARD OR REGENTS OF THE UNIVERSITY OF OKLAHOMA, Norman, OK (US)

( * ) Notice: Subject to any disclaimer, the term of this patent is extended or adjusted under 35 U.S.C. 154(b) by 256 days.

(21) Appl. No.: 16/134,696

(22) Filed: Sep. 18, 2018

(65) Prior Publication Data

US 2019/0002508 A1    Jan. 3, 2019

Related U.S. Application Data

(63) Continuation-in-part of application No. 15/081,021, filed on Mar. 25, 2016, now abandoned.

(60) Provisional application No. 62/138,781, filed on Mar. 26, 2015, provisional application No. 62/560,999, filed on Sep. 20, 2017.

(51) Int. Cl.
 *C07K 14/21* (2006.01)
 *C12Q 1/18* (2006.01)
 *C07K 14/195* (2006.01)

(52) U.S. Cl.
 CPC ............ *C07K 14/21* (2013.01); *C07K 14/195* (2013.01); *C07K 14/212* (2013.01); *C12Q 1/18* (2013.01)

(58) Field of Classification Search
 None
 See application file for complete search history.

(56) References Cited

U.S. PATENT DOCUMENTS 8,916,684 B2   12/2014  Movileanu et al.

OTHER PUBLICATIONS

Niedzwiecki et al. Biophysical Journal, vol. 103, pp. 2115-2124 Nov. 2012 (Year: 2012).*
Krewinkle et al. Journal of Nano Biotechnology vol. 9, No. 33 2011 (Year: 2011).*
Tikhonova et al. Journal of Bacteriology vol. 184, No. 23, 2002 (Year: 2002).*
Sokol et al. Infection and Immunity ,vol. 68, pp. 6554-6560, 2000 (Year: 2000).*
Sun et al. Biotecnical and Biophysical Research Communication , vol. 453, pp. 254-267, 2014 (Year: 2014).*
Jingjing et al. Biotecnical and Biophysical Research Communication , vol. 453, pp. 254-267, 2014 (Year: 2014).*
Loh, et al.; "Use of the Fluorescent Probe 1-N-Phenylnaphthylamine to Study the Interactions of Aminoglycoside Antibiotics with the Outer Membrane of Pseudomonas aeruginosa"; Antimicrobial Agents and Chemotherapy; American Society for Microbiology; vol. 26, No. 4; Oct. 1984; 546-551.
Nikaido; "Preventing drug access to targets: cell surface permeability barriers and active efflux in bacteria"; Cell & Development Biology; vol. 12; 2001; 215-223.
Killmann, et al.; "FhuA Barrel-Cork Hybrids Are Active Transporters and Receptors"; Journal of Bacteriology; vol. 183, No. 11; Jun. 2001; 3476-3487.
Braun, et al.; "Diffusion through channel derivatives of the *Escherichia coli* FhuA transport protein"; Eur. J. Biochem.; vol. 269; 2002; 4948-4959.
Tikhonova, et al; "Chimeric Analysis of the Multicomponent Multidrug Efflux Transporters from Gram-Negative Bacteria"; Journal of Bacteriology; vol. 184, No. 23; Dec. 2002; 6499-6507.
Choi, et al.; "mini-Tn7 insertion in bacteria with secondary, non-glmS-linked attTn7 sites: example Proteus mirabilis Hl4320"; Nature Protocols; vol. 1, No. 1; 2006; 170-178.
Bavro, et al.; "Assembly and Channel Opening in a Bacterial Drug Efflux Machine"; Molecular Cell; vol. 30, Apr. 11, 2008; 114-121.
Schurek, et al.; "Novel Genetic Determinants of Low-Level Aminoglycoside Resistance in Pseudomonas aeruginosa"; Antimicrobial Agents and Chemotherapy; vol. 52, No. 12; Dec. 2008; 4213-4219.
Cai, et al.; "Development of a liquid chomatography/mass spectrometry-based drug accumulation assay in Pseudomonas aeruginosa"; Analytical Biochemistry; vol. 385; 2009; 321-325.
Nagano, et al.; "Kinetic behavior of the major multidrug efflux pump AcrB of *Escherichia coli*"; PNAS; vol. 106, No. 14; Apr. 7, 2009; 5854-5858.
Krewinkel, et al.; "Engineering of an *E. coli* outer membrane protein FhuA with increased channel diameter"; Journal of Nanobiotechnology; vol. 9, No. 33; 2011; 1-8.
Muhammad, et al.; "Engineering of the *E. coli* Outer Membrane Protein FhuA to overcome the Hydrophobic Mismatch in Thick Polymeric Membranes"; Journal of Nanobiotechnology; vol. 9, No. 8; 2011; 1-9.
Mohammad, et al.; "Redesign of a Plugged β-Barrel membrane Protein"; Journal of Biological Chemistry; vol. 286, No. 10; Mar. 11, 2011; 8000-8013.
Nikaido, et al.; "Broad-specificity efflux pumps and their role in multidrug resistance of Gram-negative bacteria"; FEMS Microbiol Rev; vol. 36; 2012; 340-363.
Niedzwiecki, et al.; "Inspection of the Engineered FhuA ΔC/Δ4L Protein Nanopore by Polymer Exclusion"; Biophysical Journal; vol. 103; Nov. 2012; 2115-2124.

(Continued)

*Primary Examiner* — Jana A Hines
*Assistant Examiner* — Khatol S Shahnan Shah
(74) *Attorney, Agent, or Firm* — Parker Highlander PLLC

(57) ABSTRACT

Mutants of Gram-negative bacteria having outer membranes comprising modified OrbA nanopores absent an N-terminal plug domain are disclosed. The modified OrbA nanopores confer the outer membrane of the bacteria with enhanced permeability. The mutants of Gram-negative bacteria optionally comprise efflux-deficient efflux pumps. The mutants may be used, for example, in a screening method for identifying a compound having an anti-bacterial activity.

10 Claims, 17 Drawing Sheets
(6 of 17 Drawing Sheet(s) Filed in Color)

Specification includes a Sequence Listing.

(56) References Cited

OTHER PUBLICATIONS

Zgurskaya, et al.; "Permeability Barrier of Gram-Negative Cell Envelopes and Approaches to Bypass It"; ACS Infect Dis., vol. 1, No. 11; 2015; 512-522.
Charan, et al.; "Grafting PNIPAAm from β-barrel shaped transmembrane nanopores"; Biomaterials; vol. 107; 2016; 115-123.
Wolfe, et al.; "Global redesign of a native β-barrel scaffold"; Biochimica et Biophysica Acta; vol. 1858; 2016; 19-29.

\* cited by examiner

SEQUENCE LISTING

```
<160> NUMBER OF SEQ ID NOS: 4

<210> SEQ ID NO 1
<211> LENGTH: 1512
<212> TYPE: DNA
<213> ORGANISM: Artificial Sequence
<220> FEATURE:
<223> OTHER INFORMATION: Completely synthesized in the lab.

<400> SEQUENCE: 1
atggagtggg caaccagcac gcgcgtgcgt gcgatcgcgg cggcggcagg cgtggcgttc      60
tgcgcggcgg cgagtcatgc gcaggcacag gcgattcgcg aggtcggcgt gcaggtgggc     120
```

```
aactacgcgc gcaagcagct gatgttcgat atcggcgaca agatcgacaa ggatggcacg    180
ctgtcgtacc ggatcgtcgg cgtcggccgc gacggcaacg cgcagacggg gccgctcgcc    240
gaccagcgcg tgtcgttcgc gccgtcgctc aagtggcagc cgaacgcaaa cacgtcgctc    300
acgctcgccg cgacgtacct gcaggactgg ggcgacacgg caacagcga gggcagccac     360 taccgcaaga agcaatggtc gatcggctat cagttcgagc acaagctgaa cccggtgtgg    420
acgttccggc agaacgtgcg ctggatgcac ctggcgctcg acgacgcgtc cgtctacggc    480
aacagcgagg gcagcacgcg ctacgcgggc ctgttccagt tcaactacag ccgcttcgac    540
gtcgacaacc aggcgcaggc gaaattcacg acaggcccgt tgagccacac actgctgttc    600
ggcttcgact acaaccggca gacgacgacc gacagcgaat ggctcgcggg caacagcgag    660
ggcagcgcgt acccgcgcac cgacacgaag acgacgctca acgccttcgg cctgtacgtg    720
caggaccaga tcaagtggca cgctgggtg ctcacgctcg gcggccggca ggactggacg     780
cgcacgtcgc aggacgacat cgcgaactcg gcgagcttca gcagaacga ccacgcgttc      840 agcgggcgcg tcggcctgac ctatctcggc gattacggcc tcgcgccgta cctcagctat    900
tcgacgtcgt tcaatccgca gatcggcgtg ggcggcgggc gccagatcga ggctggcctg    960
cgctggcagc cgccgggcaa gaacctgatg ctgaacgcgg ccgtctacca gatcaaccag   1020
acgaacgtcg cgatgagcaa tccgaacgat ccgacgagca gcacgttcgt gcaggtgggc   1080
gaggtgcgct cgcgcggcgt cgagctgagc gcggtgggca acctgtcgcg cgagctgtcg   1140
gtgatcgccg cgtacgtcta tcaggacgtg aagaacgtgc aggcgaatga caacacgctg   1200
aacaagtggc ccgtcgacgt gccgcgcccg cgccagatcg cgtcgctgtg ggccgactgg   1260
acgtggcgca acgggccgct cacgggcttc ggcgtcggcg ccggcgtgcg ctacatgggc   1320
aacagcgagg gcagcagcta cacgctgttc gacgcggcgc tgcactacga gctgcgcaac   1380
tggcgcttcg cgctcaatgc gacgaacctg ggcaacagcg agggcagccg caccgtgatc   1440
gcgacggcga aatacaactg gctggtgccg cgcggcagcc accaccatca ccaccatcac   1500
caccatcact ga                                                        1512
```

<210> SEQ ID NO 2
<211> LENGTH: 503
<212> TYPE: PRT
<213> ORGANISM: Artificial Sequence
<220> FEATURE:
<223> OTHER INFORMATION: Completely synthesized in the lab.

<400> SEQUENCE: 2

```
Met Glu Trp Ala Thr Ser Thr Arg Val Arg Ala Ile Ala Ala Ala Ala
1               5                   10                  15

Gly Val Ala Phe Cys Ala Ala Ala Ser His Ala Gln Ala Gln Ala Ile
            20                  25                  30

Arg Glu Val Gly Val Gln Val Gly Asn Tyr Ala Arg Lys Gln Leu Met
        35                  40                  45

Phe Asp Ile Gly Asp Lys Ile Asp Lys Asp Gly Thr Leu Ser Tyr Arg
    50                  55                  60

Ile Val Gly Val Gly Arg Asp Gly Asn Ala Gln Thr Gly Pro Leu Ala
65                  70                  75                  80

Asp Gln Arg Val Ser Phe Ala Pro Ser Leu Lys Trp Gln Pro Asn Ala
                85                  90                  95

Asn Thr Ser Leu Thr Leu Ala Ala Thr Tyr Leu Gln Asp Trp Gly Asp
            100                 105                 110
```

```
Thr Gly Asn Ser Glu Gly Ser His Tyr Arg Lys Lys Gln Trp Ser Ile
            115                 120                 125
Gly Tyr Gln Phe Glu His Lys Leu Asn Pro Val Trp Thr Phe Arg Gln
130                 135                 140
Asn Val Arg Trp Met His Leu Ala Leu Asp Asp Ala Ser Val Tyr Gly
145                 150                 155                 160
Asn Ser Glu Gly Ser Thr Arg Tyr Ala Gly Leu Phe Gln Phe Asn Tyr
                165                 170                 175
Ser Arg Phe Asp Val Asp Asn Gln Ala Gln Ala Lys Phe Thr Thr Gly
            180                 185                 190
Pro Leu Ser His Thr Leu Leu Phe Gly Phe Asp Tyr Asn Arg Gln Thr
            195                 200                 205
Thr Thr Asp Ser Glu Trp Leu Ala Gly Asn Ser Glu Gly Ser Ala Tyr
210                 215                 220
Pro Arg Thr Asp Thr Lys Thr Thr Leu Asn Ala Phe Gly Leu Tyr Val
225                 230                 235                 240
Gln Asp Gln Ile Lys Trp Gln Arg Trp Val Leu Thr Leu Gly Gly Arg
                245                 250                 255
Gln Asp Trp Thr Arg Thr Ser Gln Asp Asp Ile Ala Asn Ser Ala Ser
            260                 265                 270
Phe Lys Gln Asn Asp His Ala Phe Ser Gly Arg Val Gly Leu Thr Tyr
            275                 280                 285
Leu Gly Asp Tyr Gly Leu Ala Pro Tyr Leu Ser Tyr Ser Thr Ser Phe
            290                 295                 300
Asn Pro Gln Ile Gly Val Gly Gly Arg Gln Ile Glu Ala Gly Leu
305                 310                 315                 320
Arg Trp Gln Pro Pro Gly Lys Asn Leu Met Leu Asn Ala Ala Val Tyr
                325                 330                 335
Gln Ile Asn Gln Thr Asn Val Ala Met Ser Asn Pro Asn Asp Pro Thr
            340                 345                 350
Ser Ser Thr Phe Val Gln Val Gly Glu Val Arg Ser Arg Gly Val Glu
            355                 360                 365
Leu Ser Ala Val Gly Asn Leu Ser Arg Glu Leu Ser Val Ile Ala Ala
370                 375                 380
Tyr Val Tyr Gln Asp Val Lys Asn Val Gln Ala Asn Asp Asn Thr Leu
385                 390                 395                 400
Asn Lys Trp Pro Val Asp Val Pro Arg Pro Arg Gln Ile Ala Ser Leu
                405                 410                 415
Trp Ala Asp Trp Thr Trp Arg Asn Gly Pro Leu Thr Gly Phe Gly Val
            420                 425                 430
Gly Ala Gly Val Arg Tyr Met Gly Asn Ser Glu Gly Ser Ser Tyr Thr
            435                 440                 445
Leu Phe Asp Ala Ala Leu His Tyr Glu Leu Arg Asn Trp Arg Phe Ala
450                 455                 460
Leu Asn Ala Thr Asn Leu Gly Asn Ser Glu Gly Ser Arg Thr Val Ile
465                 470                 475                 480
Ala Thr Ala Lys Tyr Asn Trp Leu Val Pro Arg Gly Ser His His
                485                 490                 495
His His His His His His
            500

<210> SEQ ID NO 3
<211> LENGTH: 487
<212> TYPE: PRT
```

<213> ORGANISM: Artificial Sequence
<220> FEATURE:
<223> OTHER INFORMATION: Completely synthesized in the lab.

<400> SEQUENCE: 3

```
Met Glu Trp Ala Thr Ser Thr Arg Val Arg Ala Ile Ala Ala Ala
1               5                   10                  15

Gly Val Ala Phe Cys Ala Ala Ser His Ala Gln Ala Gln Ala Ile
            20                  25                  30

Arg Glu Val Gly Val Gln Val Gly Asn Tyr Ala Arg Lys Gln Leu Met
        35                  40                  45

Phe Asp Ile Gly Asp Lys Ile Asp Lys Asp Gly Thr Leu Ser Tyr Arg
50                  55                  60

Ile Val Gly Val Gly Arg Asp Gly Asn Ala Gln Thr Gly Pro Leu Ala
65                  70                  75                  80

Asp Gln Arg Val Ser Phe Ala Pro Ser Leu Lys Trp Gln Pro Asn Ala
                85                  90                  95

Asn Thr Ser Leu Thr Leu Ala Ala Thr Tyr Leu Gln Asp Trp Gly Asp
            100                 105                 110

Thr Gly Asn Ser Glu Gly Ser His Tyr Arg Lys Lys Gln Trp Ser Ile
        115                 120                 125

Gly Tyr Gln Phe Glu His Lys Leu Asn Pro Val Trp Thr Phe Arg Gln
130                 135                 140

Asn Val Arg Trp Met His Leu Ala Leu Asp Asp Ala Ser Val Tyr Gly
145                 150                 155                 160

Asn Ser Glu Gly Ser Thr Arg Tyr Ala Gly Leu Phe Gln Phe Asn Tyr
                165                 170                 175

Ser Arg Phe Asp Val Asp Asn Gln Ala Gln Ala Lys Phe Thr Thr Gly
            180                 185                 190

Pro Leu Ser His Thr Leu Leu Phe Gly Phe Asp Tyr Asn Arg Gln Thr
        195                 200                 205

Thr Thr Asp Ser Glu Trp Leu Ala Gly Asn Ser Glu Gly Ser Ala Tyr
210                 215                 220

Pro Arg Thr Asp Thr Lys Thr Thr Leu Asn Ala Phe Gly Leu Tyr Val
225                 230                 235                 240

Gln Asp Gln Ile Lys Trp Gln Arg Trp Val Leu Thr Leu Gly Gly Arg
                245                 250                 255

Gln Asp Trp Thr Arg Thr Ser Gln Asp Asp Ile Ala Asn Ser Ala Ser
            260                 265                 270

Phe Lys Gln Asn Asp His Ala Phe Ser Gly Arg Val Gly Leu Thr Tyr
        275                 280                 285

Leu Gly Asp Tyr Gly Leu Ala Pro Tyr Leu Ser Tyr Ser Thr Ser Phe
290                 295                 300

Asn Pro Gln Ile Gly Val Gly Gly Arg Gln Ile Glu Ala Gly Leu
305                 310                 315                 320

Arg Trp Gln Pro Pro Gly Lys Asn Leu Met Leu Asn Ala Ala Val Tyr
                325                 330                 335

Gln Ile Asn Gln Thr Asn Val Ala Met Ser Asn Pro Asn Asp Pro Thr
            340                 345                 350

Ser Ser Thr Phe Val Gln Val Gly Glu Val Arg Ser Arg Gly Val Glu
        355                 360                 365

Leu Ser Ala Val Gly Asn Leu Ser Arg Glu Leu Ser Val Ile Ala Ala
370                 375                 380

Tyr Val Tyr Gln Asp Val Lys Asn Val Gln Ala Asn Asp Asn Thr Leu
```

```
                385                 390                 395                 400
Asn Lys Trp Pro Val Asp Val Pro Arg Pro Arg Gln Ile Ala Ser Leu
            405                 410                 415

Trp Ala Asp Trp Thr Trp Arg Asn Gly Pro Leu Thr Gly Phe Gly Val
            420                 425                 430

Gly Ala Gly Val Arg Tyr Met Gly Asn Ser Glu Gly Ser Ser Tyr Thr
            435                 440                 445

Leu Phe Asp Ala Ala Leu His Tyr Glu Leu Arg Asn Trp Arg Phe Ala
450                 455                 460

Leu Asn Ala Thr Asn Leu Gly Asn Ser Glu Gly Ser Arg Thr Val Ile
465                 470                 475                 480

Ala Thr Ala Lys Tyr Asn Trp
            485

<210> SEQ ID NO 4
<211> LENGTH: 7877
<212> TYPE: DNA
<213> ORGANISM: Artificial Sequence
<220> FEATURE:
<223> OTHER INFORMATION: Completely synthesized in the lab.

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct agaggaccag ccgcgtaacc tggcaaaatc ggttacggtt gagtaataaa      360
tggatgccct gcgtaagcgg gtgtgggcgg acaataaagt cttaaactga caaaataga      420 tctaaactat gacaataaag tcttaaacta gacagaatat tgtaaactg aaatcagtcc      480 agttatgctg tgaaaaagca tactggactt tgttatggc taaagcaaac tcttcatttt      540
ctgaagtgca aattgcccgt cgtattaaag aggggcgtgg ggttcgaggt cgacggtatc      600
gataagctag cttaattagc tgagcttgga ctcctgttga tagatccagt aatgacctca      660
gaactccatc tggatttgtt cagaacgctc ggttgccgcc gggcgttttt tattggtgag      720
aatccaagct agactgcgat gagtggcagg gcggggcgta atttttttaa ggcagttatt      780
ggtgccctta aacgcctggg gtaatgactc tctagcttga ggcatcaaat aaaacgaaag      840
gctcagtcga aagactgggc ctttcgtttt atctgttgtt tgtcggtgaa cgctctcctg      900
agtaggacaa atccgccgct aggagcttgc ggcccggacg atgagctcga attggggatc      960
ttgaagtacc tattccgaag ttcctattct ctagaaagta taggaacttc agagcgcttt     1020
tgaagctgat gtgcttaaaa acttactcaa tggaataatt ctagataatt cttaggccac     1080
acgttcaagt gcagccacag gataaatttg cactgagcct gggtgggatt cggactcgac     1140
cgcatagcct tcaggagtga gttttgtgca ataccaaccg acgacttgac cctgccaagc     1200
ggcaccagat ttcttgcgta cgcgatcccc taagccaaag gtggcactca ggggaagcgc     1260
aaactgccct gcaacgggag cgttggcttc atcgctactt tgacccatgt cgaatccttc     1320
ttgtgaatct attatggcga caagcaaatc gagctctgac tgcctacccc acaacaacta     1380
tcagaaagca ccagcacaac ggctgcctaa ctttgtttta gggcgactgc cctgctgcgt     1440
aacatcgttg ctgctcccata acatcaaaca tcgacccacg gcgtaacgcg cttgctgctt     1500
```

```
ggatgcccga ggctagactg tacaaaaaaa cagtcataac aagccatgaa aaccgccact   1560
gcgccgttac caccgctgcg ttcggtcaag gttctggacc agttgcgtga gcgcatacgc   1620
tacttgcatt acagtttacg aaccgaacag gcttatgtca actgggttcg tgaattatcc   1680
attgctgttg acaaagggaa tcaggggatc ttgaagttcc tattccgaag ttcctattct   1740
ctagaaagta taggaacttc agagcgcttt tgaagctaat tcgagctcga tcatgcattt   1800
aatctttctg cgaattgaga tgacgccact ggctgggcgt catcccggtt tcccgggtaa   1860
acaccaccga aaatagtta ctatcttcaa agccacattc ggtcgaaata tcactgatta   1920
acaggcggct atgctggaga agatattgcg catgacacac tctgacctgt cgcagatatt   1980
gattgatggt cattccagtc tgctggcgaa attgctgacg caaaacgcgc tcactgcacg   2040
atgcctcatc acaaaattta tccagcgcaa agggactttt caggctagcc gccagccggg   2100
taatcagctt atccagcaac gtttcgctgg atgttggcgg caacgaatca ctggtgtaac   2160
gatggcgatt cagcaacatc accaactgcc cgaacagcaa ctcagccatt tcgttagcaa   2220
acggcacatg ctgactactt tcatgctcaa gctgaccgat aacctgccgc gcctgcgcca   2280
tccccatgct acctaagcgc cagtgtggtt gccctgcgct ggcgttaaat cccggaatcg   2340 cccccctgcca gtcaagattc agcttcagac gctccgggca ataaataata ttctgcaaaa   2400
ccagatcgtt aacggaagcg taggagtgtt tatcgtcagc atgaatgtaa aagagatcgc   2460
cacgggtaat gcgataaggg cgatcgttga gtacatgcag gccattaccg cgccagacaa   2520
tcaccagctc acaaaaatca tgtgtatgtt cagcaaagac atcttgcgga taacggtcag   2580
ccacagcgac tgcctgctgg tcgctggcaa aaaaatcatc tttgagaagt tttaactgat   2640
gcgccaccgt ggctacctcg gccagagaac gaagttgatt attcgcaata tggcgtacaa   2700
atacgttgag aagattcgcg ttattgcaga aagccatccc gtccctggcg aatatcacgc   2760
ggtgaccagt taaactctcg gcgaaaaagc gtcgaaaagt ggttactgtc gctgaatcca   2820
cagcgatagg cgatgtcagt aacgctggcc tcgctgtggc gtagcagatg tcgggctttc   2880
atcagtcgca ggcggttcag gtatcgctga ggcgtcagtc ccgtttgctg cttaagctgc   2940
cgatgtagcg tacgcagtga aagagaaaat tgatccgcca cggcatccca attcacctca   3000
tcggcaaaat ggtcctccag ccaggccaga agcaagttga gacgtgatgc gctgttttcc   3060
aggttctcct gcaaactgct tttacgcagc aagagcagta attgcataaa caagatctcg   3120
cgactggcgg tcgagggtaa atcattttcc ccttcctgct gttccatctg tgcaaccagc   3180
tgtcgcacct gctgcaatac gctgtggtta acgcgccagt gagacggata ctgcccatcc   3240
agctcttgtg gcagcaactg attcagcccg gcgagaaact gaaatcgatc cggcgagcga   3300
tacagcacat tggtcagaca cagattatcg gtatgttcat acagatgccg atcatgatcg   3360
cgtacgaaac agaccgtgcc accggtgatg gtatagggct gcccattaaa cacatgaata   3420
cccgtgccat gttcgacaat cacaatttca tgaaaatcat gatgatgttc aggaaaatcc   3480
gcctgcggga gccggggttc tatcgccacg gacgcgttac cagacggaaa aaaatccaca   3540
ctatgtaata cggtcatact ggcctcctga tgtcgtcaac acggcgaaat agtaatcacg   3600
aggtcaggtt cttaccttaa attttcgacg gaaaccacg taaaaaacgt cgatttttca   3660
agatacagcg tgaattttca ggaaatgcgg tgagcatcac atcaccacaa ttcagcaaat   3720
tgtgaacatc atcacgttca tctttccctg gttgccaatg gcccatttc ctgtcagtaa   3780 cgagaaggtc gcgaattcag gcgctttta gactggtcgt aatgaaattc agcaggatca   3840
```

```
caccatggag tgggcaacca gcacgcgcgt gcgtgcgatc gcggcggcgg caggcgtggc    3900
gttctgcgcg gcggcgagtc atgcgcaggc acaggcgatt cgcgaggtcg gcgtgcaggt    3960
gggcaactac gcgcgcaagc agctgatgtt cgatatcggc gacaagatcg acaaggatgg    4020
cacgctgtcg taccggatcg tcggcgtcgg ccgcgacggc aacgcgcaga cggggccgct    4080
cgccgaccag cgcgtgtcgt tcgcgccgtc gctcaagtgg cagccgaacg caaacacgtc    4140
gctcacgctc gccgcgacgt acctgcagga ctggggcgac acgggcaaca gcagggcag    4200 ccactaccgc aagaagcaat ggtcgatcgg ctatcagttc gagcacaagc tgaacccggt    4260
gtggacgttc cggcagaacg tgcgctggat gcacctggcg ctcgacgacg cgtccgtcta    4320
cggcaacagc gagggcagca cgcgctacgc gggcctgttc cagttcaact acagccgctt    4380
cgacgtcgac aaccaggcgc aggcgaaatt cacgacaggc ccgttgagcc acacactgct    4440
gttcggcttc gactacaacc ggcagacgac gaccgacagc gaatggctcg cgggcaacag    4500
cgagggcagc gcgtacccgc gcaccgacac gaagacgacg ctcaacgcct tcggcctgta    4560
cgtgcaggac cagatcaagt ggcagcgctg ggtgctcacg ctcggcggcc ggcaggactg    4620
gacgcgcacg tcgcaggacg acatcgcgaa ctcggcgagc ttcaagcaga acgaccacgc    4680
gttcagcggg cgcgtcggcc tgacctatct cggcgattac ggcctcgcgc cgtacctcag    4740
ctattcgacg tcgttcaatc cgcagatcgg cgtgggcggc gggcgccaga tcgaggctgg    4800
cctgcgctgg cagccgccgg gcaagaacct gatgctgaac cgggccgtct accagatcaa    4860
ccagacgaac gtcgcgatga gcaatccgaa cgatccgacg agcagcacgt cgtgcaggt    4920 gggcgaggtg cgctcgcgcg cgtcgagct gagcgcggtg gcaacctgt cgcgcgagct    4980 gtcggtgatc gccgcgtacg tctatcagga cgtgaagaac gtgcaggcga atgacaacac    5040
gctgaacaag tggcccgtcg acgtgccgcg cccgcgccag atcgcgtcgc tgtgggccga    5100
ctggacgtgg cgcaacgggc cgctcacggg cttcggcgtc ggcgccggcg tgcgctacat    5160
gggcaacagc gagggcagca gctacacgct gttcgacgcg gcgctgcact acgagctgcg    5220
caactggcgc ttcgcgctca atgcgacgaa cctgggcaac agcgagggca ccgcaccgt    5280 gatcgcgacg gcgaaataca actggctggt gccgcgcggc agccaccacc atcaccacca    5340
tcaccaccat cactgaagct tgggcccggt acctcgcgaa ggccttgcag gccaaccaga    5400
taagtgaaat ctagttccaa actatttgt catttttaat tttcgtatta gcttacgacg    5460
ctacacccag ttcccatcta ttttgtcact cttccctaaa taatccttaa aaactccatt    5520
tccacccctc ccagttccca actatttgt ccgcccacag cggggcattt ttcttcctgt    5580
tatgtttggg cgctgcatta atgaatcggc caacgcgcgg ggagaggcgg tttgcgtatt    5640
gggcgctctt ccgcttcctc gctcactgac ccgctgcgct cggtcgttcg gctgcggcga    5700
gcggtatcag agcttatcgg ccagcctcgc agagcaggat tccgttgag caccgccagg    5760 tgcgaataag ggacagtgaa gaaggaacac ccgctcgcgg gtgggcctac ttcacctatc    5820
ctgcccggct gacgccgttg gatacaccaa ggaaagtcta cacgaaccct ttggcaaaat    5880
cctgtatatc gtgcgaaaaa ggatggatat accgaaaaaa tcgctataat gaccccgaag    5940
cagggttatg cagcggaaag tataccttaa ggaatcccct gataacgcag gaaagaacat    6000
gtgagcaaaa ggccagcaaa aggccaggaa ccgtaaaaag gccgcgttgc tggcgttttt    6060
ccataggctc cgcccccctg acgagcatca caaaaatcga cgctcgagtc agaggtggcg    6120
aaacccgaca ggactataaa gataccaggc gtttccccct ggaagctccc tcgtgcgctc    6180
tcctgttccg accctgccgc ttaccggata cctgtccgcc tttctccctt cgggaagcgt    6240
```

```
ggcgctttct catagctcac gctgtaggta tctcagttcg gtgtaggtcg ttcgctccaa    6300
gctgggctgt gtgcacgaac ccccgttca gcccgaccgc tgcgccttat ccggtaacta    6360
tcgtcttgag tccaacccgg taagacacga cttatcgcca ctggcagcag ccactggtaa    6420
caggattagc agagcgaggt atgtaggcgg tgctacagag ttcttgaagt ggtggcctaa    6480
ctacggctac actagaagga cagtatttgg tatctgcgct ctgctgaagc cagttacctt    6540
cggaaaaaga gttggtagct cttgatccgg caaacaaacc accgctggta gcggtggttt    6600
ttttgtttgc aagcagcaga ttacgcgcag aaaaaaagga tctcaagaag atcctttgat    6660
cttttctacg gggtctgacg ctcagtggaa cgaaaactca cgttaaggga ttttggtcat    6720
gagattatca aaaaggatct tcacctagat ccttttaaat taaaaatgaa gttttaaatc    6780
aatctaaagt atatatgagt aaacttggtc tgacagttac caatgcttaa tcagtgaggc    6840
acctatctca gcgatctgtc tatttcgttc atccatagtt gcctgactcc ccgtcgtgta    6900
gataactacg atacgggagg gcttaccatc tggccccagt gctgcaatga taccgcgaga    6960
cccacgctca ccggctccag atttatcagc aataaaccag ccagccggaa gggccgagcg    7020
cagaagtggt cctgcaactt tatccgcctc catccagtct attaattgtt gccgggaagc    7080
tagagtaagt agttcgccag ttaatagttt gcgcaacgtt gttgccattg ctacaggcat    7140
cgtggtgtca cgctcgtcgt ttggtatggc ttcattcagc tccggttccc aacgatcaag    7200
gcgagttaca tgatccccca tgttgtgcaa aaaagcggtt agctccttcg gtcctccgat    7260
cgttgtcaga agtaagttgg ccgcagtgtt atcactcatg gttatggcag cactgcataa    7320
ttctcttact gtcatgccat ccgtaagatg cttttctgtg actggtgagt actcaaccaa    7380
gtcattctga gaatagtgta tgcggcgacc gagttgctct tgcccggcgt caatacggga    7440
taataccgcg ccacatagca gaactttaaa agtgctcatc attggaaaac gttcttcggg    7500
gcgaaaactc tcaaggatct taccgctgtt gagatccagt tcgatgtaac ccactcgtgc    7560
acccaactga tcttcagcat cttttacttt caccagcgtt tctgggtgag caaaaacagg    7620
aaggcaaaat gccgcaaaaa agggaataag ggcgacacgg aaatgttgaa tactcatact    7680 cttcctttt caatattatt gaagcattta tcagggttat tgtctcatga gcggatacat    7740
atttgaatgt atttagaaaa ataaacaaat aggggttccg cgcacatttc cccgaaaagt    7800
gccacctgac gtctaagaaa ccattattat catgacatta acctataaaa ataggcgtat    7860
cacgaggccc tttcgtc                                                  7877
```

PORE-MODIFIED GRAM-NEGATIVE BACTERIA AND USES THEREOF

CROSS REFERENCE TO RELATED APPLICATIONS/INCORPORATION BY REFERENCE STATEMENT

The present patent application is a continuation-in-part of U.S. patent application Ser. No. 15/081,021, filed Mar. 25, 2016, which claims priority to U.S. Provisional Patent Application U.S. Ser. No. 62/138,781, filed on Mar. 26, 2015. The present patent application also claims priority to U.S. Provisional Patent Application U.S. Ser. No. 62/560,999, filed on Sep. 20, 2017. The entire contents of each of said applications is hereby expressly incorporated herein by reference.

GOVERNMENT SUPPORT

This invention was made with government support under Grant number HDTRA1-14-1-0019-P00002 awarded by the Defense Threat Reduction Agency of the Department of Defense. The government has certain rights in the invention.

BACKGROUND

In recent years, antibiotic-resistant Gram-negative bacterial species emerged in clinics and cause life-threatening infections that are effectively untreatable by antibiotic monotherapy. These species are intrinsically resistant to antibiotics, albeit to a varying degree, and gain further resistance when exposed to antibiotic treatments. The differences in antibiotic susceptibilities among Gram-negative bacteria are attributed to various factors including the presence of chromosomally encoded enzymes that modify antibiotics, mutations, and variations in activities or amounts of antibiotic targets. Additionally, in all Gram-negative species, the low permeability barrier of the outer membranes and multidrug efflux play key roles in resisting antibiotic challenges.

The outer membrane (OM) of Gram-negative bacteria is an asymmetric bilayer composed of lipopolysaccharides (LPS) in the outer leaflet and glycerophospholipids (PL) in the inner leaflet. The major features of the LPS structure, such as the presence of lipid A, the core and O-antigen chains, are conserved among various species while specific chemical structures vary broadly (FIGS. 1A-C). The different LPS aggregate into species-specific LPS-PL bilayers with a variable number of LPS molecules, thicknesses, surface charge distributions and dynamics. These features, in turn, translate into differences in the permeability properties of LPS-PL bilayers. Most of the current knowledge on selectivity of the OM permeability barriers is based on extensive studies of model organisms such as *Escherichia coli*. In enteric bacteria, antibacterial activities of large and polar antibiotics exceeding the size of general porins (>600 Da in *E. coli*) are usually the most restricted by OM, whereas the zwitterionic character in compounds correlates with increased permeation across the OM.

The inner membrane (IM) is relatively permeable for a majority of amphiphilic drug molecules. However, it contains multidrug efflux pumps responsible for active non-specific extrusion of toxic compounds from cells. Two types of efflux pumps operate and affect drug concentrations in different bacterial cell compartments. Some efflux transporters transport drugs across the IM and affect the cytoplasmic drug accumulation. Other transporters, such as those belonging to the Resistance-Nodulation-cell Division (RND) superfamily, associate with additional proteins located in the periplasm and in the OM and function as trans-envelope (across the two membranes) efflux pumps. These efflux pumps bind various substrates on the periplasmic side of the IM and translocate them across the OM into the external medium. Inactivation of trans-envelope efflux increases bacterial susceptibility to various antibiotics, whereas their overexpression is a recognized cause of the clinical antibiotic resistance. Studies that included such Gram-negative bacteria as *Haemophilus influenzae*, *E. coli* and *P. aeruginosa*, revealed that antibacterial activities of the very polar and low molecular weight (MW) compounds on one hand, and zwitterionic and high MW compounds on the other, tend to be the least affected by efflux pumps, suggesting that such compounds are poor substrates for multidrug transporters. In contrast, an increase in hydrophobicity was found to correlate with increased propensity of a compound to be a substrate of efflux pumps in studies of *Salmonella typhimurium*.

The exceptional efficiency of trans-envelope efflux pumps is the result of a complex interplay between the two opposing fluxes of drugs across the two membranes. The experimental data and kinetic modeling agree that Gram-negative cell envelopes serve to dramatically reduce the intracellular concentration of many antibiotics unless breached by either efflux inactivation or an increase in the transmembrane flux (Krishnamoorthy G, Wolloscheck D, Weeks J W, Croft C, Rybenkov V V, Zgurskaya H I. 2016, Breaking the Permeability Barrier of *Escherichia coli* by Controlled Hyperporination of the Outer Membrane. Antimicrob Agents Chemother 60:7372-7381; Nichols W W. 2017, Modeling the kinetics of the permeation of antibacterial agents into growing bacteria and its interplay with efflux. Antimicrob Agents Chemother doi:10.1128/AAC.02576-16). This synergistic character and effectiveness of cell envelopes create a major hurdle in the discovery and development of new therapeutics against Gram-negative pathogens. Significant efforts are presently directed at gaining a fundamental understanding of the permeability properties of the OM and at finding correlations between physicochemical properties of compounds and their permeation across cell envelopes. The task is complicated by difficulties in separation of contributions of diffusion and active efflux in antibacterial activities. Furthermore, heuristics established using model organisms, such as *E. coli*, tend to be poorly applicable to other Gram-negative bacteria and clinical isolates.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure. The patent or application file contains at least one drawing executed in color. Copies of this patent or patent application publication with color drawing(s) will be provided by the Office upon request and payment of the necessary fee.

DETAILED DESCRIPTION

Figure 1A:
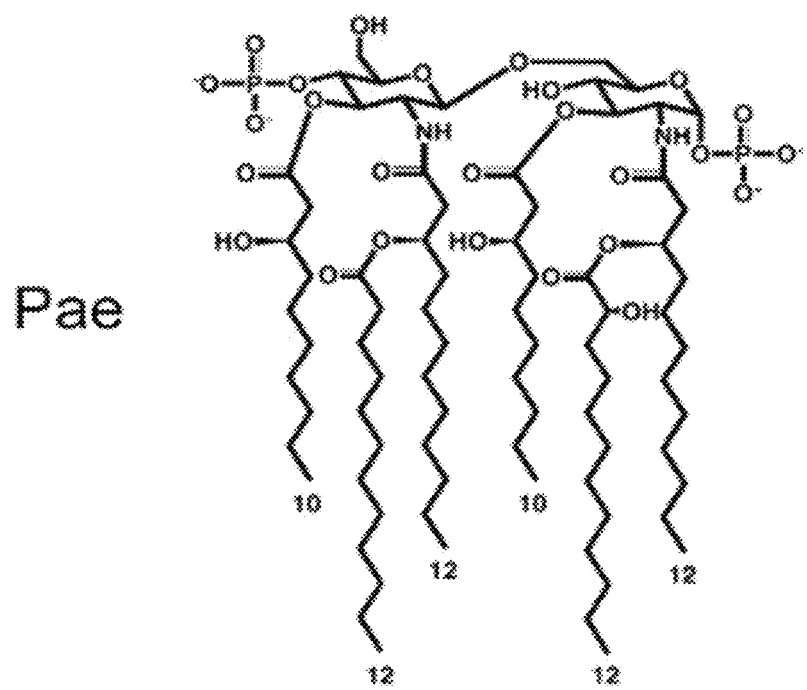
FIG. 1A shows structures of lipid A moieties and hyperporination of the outer membrane of a *P. aeruginosa* mutant constructed in accordance with the present disclosure. The immunoblotting analyses with a monoclonal anti-His antibody, the copy number of the expressed hyperpores per cell, and MICs of vancomycin (VAN) in the induced cells are shown.
Figure 1A:
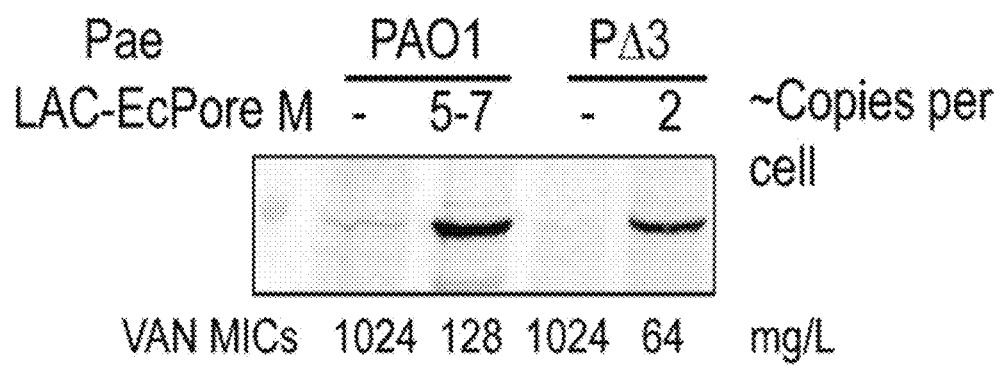

Gram-negative bacteria are notoriously resistant to antibiotics, but the extent of the resistance varies broadly between species. Multidrug resistant strains of Gram-negative pathogens rapidly spread in clinics. Significant efforts worldwide are currently directed to finding the rules of permeation of antibiotics across two membrane envelopes of these bacteria. We have developed an approach that separates the contributions of active efflux and passive barrier in activities of antibiotics and thereby sidesteps many of the aforementioned difficulties (Krishnamoorthy et al., 2016, op cit.). In this approach, a modified FhuA siderophore uptake channel (EcPore) is expressed from the chromosome and used to create a plurality of large non-specific pores in the OM of *E. coli*. EcPore is large enough for a passage of small proteins and does not discriminate between compounds based on their hydrophilicity (Krishnamoorthy et al., 2016, op cit.).

In the present disclosure additional results regarding the permeability barriers of four Gram-negative species *P. aeruginosa, Acinetobacter baumannii, Burkholderia cepacia* and *B. thailandensis* are provided. These bacteria were chosen because they are difficult to treat clinically and differ significantly in antibiotic susceptibilities, the structure and composition of their OM and in the activities and repertoire of trans-envelope efflux pumps. Thus, they represent a diverse spectrum spanning the types of Gram-negative cell envelopes. We constructed hyperporinated *P. aeruginosa* and *A. baumannii* using EcPore. Hyperporinated strains of *B. thailandensis* and *B. cepacia* were constructed using a mutant OrbA protein. We analyzed the contributions of the OM permeability and intrinsic active efflux in antibacterial activities of antibiotics belonging to different classes in all strains. Antibacterial activities were then correlated with permeability barriers that differ in chemical structures and properties.

The present disclosure thus describes work wherein major differences in antibacterial activities that distinguish the permeability barriers of *P. aeruginosa, A. baumannii, B. thailandensis* and *B. cepacia* were identified. We unexpectedly found that synergistic interplays between active efflux pumps and passive barriers (the OM barrier) universally protect Gram-negative bacteria from structurally diverse antibiotics, even those previously thought to be privileged in efflux avoidance. We report that in significant human pathogens including *Acinetobacter baumannii, Pseudomonas aeruginosa* and *Burkholderia* spp, the differences in antibiotic resistance are largely defined by their penetration into the cell. For all tested antibiotics, the intracellular penetration was determined by a synergistic relationship between active efflux and the permeability barrier. We found that the outer membrane and efflux pumps select compounds based on distinct properties and together universally protect bacteria from structurally diverse antibiotics. Based on their permeation properties, antibiotics can be divided into four clusters. Within each cluster, antibiotics are characterized by their own sets of structural rules, which are defined by their interactions with the permeability barrier. The identified specificities in the permeability barriers can be used to design successful therapeutic strategies against antibiotic resistant pathogens.

The diversity of the outer membrane structures and efflux capacities included in this study broaden the diversity of antibiotics affected by active efflux and outer membrane barriers and define the clustering of antibiotics according to specific biological determinants such as requirement of specific porins in the OM, targeting the OM or specific recognition by efflux pumps. Despite the lack of apparent chemical similarities, antibiotics within each cluster are likely to share structural characteristics that are recognized by distinct permeability barriers. These characteristics define the rules of antibiotic permeation into Gram-negative bacteria.

Therefore, disclosed herein are novel bacterial mutants (i.e., mutants which are pore-modified and/or efflux-pump-modified) which have been sensitized, for example for drug discovery, drug screening, structure-activity relationships and development purposes. More particularly, the present disclosure includes embodiments of Gram-negative bacteria which have been sensitized to biologically active compounds by introducing modified nanopores in the outer membranes thereby modulating permeability properties of the outer membranes without compromising active efflux. The present disclosure also includes embodiments of Gram-negative bacteria which have been sensitized to biologically active compounds by introducing modified efflux pumps thereby modulating active efflux properties of the cells without compromising OM permeability. Other embodiments include Gram-negative bacteria which have been sensitized by introducing modified nanopores in the outer membranes thereby modulating permeability properties of the outer membranes and which include modified efflux pumps thereby modulating active efflux properties of the cells. Certain embodiments of the present disclosure are directed to *P. aeruginosa, A. baumannii, B. thailandensis* and *B. cepacia* strains, as well as other strains that are sensitized to antibiotics in a controlled manner due to increased rates of antibiotic uptake without compromising the active efflux and cell viability. This was carried out by inserting into bacterial chromosomes genes encoding modified protein nanopores. These nanopores can be produced in a tightly controlled manner so that the outer membranes of the bacterial cells have different total numbers of nanopores depending on the concentration of an inducer present in the external medium. In at least one non-limiting embodiment, the nanopore is OrbA ΔC/Δ4L, a genetically modified OrbA variant without its N-terminal plug (cork) domain and without four of its large external loops. These nanopores, when present in the outer membrane, remove restrictions on the size and physico-chemical properties of compounds that can penetrate the outer membrane without compromising drug efflux activities or physiological states of cells. We demonstrated the modulation of the outer membrane permeability by: (i) measuring changes in susceptibilities of bacterial cells with nanopores to antibiotics as a dependence on the concentration of an inducer; (ii) measuring accumulation of radioactive chemicals of different sizes and fluorescent probes in cells containing nanopores. Thus, described herein is the development of bacterial strains, in which permeation properties of the outer membrane and hence uptake of antibiotics and other molecules can be controlled.

The present patent application contains subject matter related to U. S. Provisional Patent Application Ser. No. 62/138,781, filed on Mar. 26, 2015, and to U.S. patent application Ser. No. 15/081,021, filed Mar. 25, 2016, the entire contents of which are hereby expressly incorporated herein by reference.

Before describing various embodiments of the present disclosure in more detail by way of exemplary description, examples, and results, it is to be understood that the present disclosure is not limited in application to the details of methods and compositions as set forth in the following description. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that other embodiments of the inventive concepts may be practiced without these specific details. In other instances, features which are well known to persons of ordinary skill in the art have not been described in detail to avoid unnecessary complication of the description.

While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit and scope of the inventive concepts. All such similar substitutes and modifications apparent to those of skilled in the art are deemed to be within the spirit, scope and concept of the present disclosure as described herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study objects. Further, in this detailed description and the appended claims, each numerical value (e.g., temperature or time) should be read once as modified by the term "about" (unless already expressly so modified), and then read again as not so modified unless otherwise indicated in context. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

Also, any range listed or described herein is intended to include, implicitly or explicitly, any number within the range, particularly all integers, including the end points, and is to be considered as having been so stated. For example, "a range from 1 to 10" is to be read as indicating each possible number, particularly integers, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1). Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 1-20, 10-50, 50-100, 100-1,000, 1,000-3,000, 2,000-4,000, etc.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

Specific amino acids may be referred to herein by the following designations: alanine: ala or A; arginine: arg or R; asparagine: asn or N; aspartic acid: asp or D; cysteine: cys or C; glutamic acid: glu or E; glutamine: gln or Q; glycine: gly or G; histidine: his or H; isoleucine: ile or I; leucine: leu or L; lysine: lys or K; methionine: met or M; phenylalanine: phe or F; proline: pro or P; serine: ser or S; threonine: thr or T; tryptophan: trp or W; tyrosine: tyr or Y; and valine: val or V.

For purposes of classifying amino acids substitutions as conservative or nonconservative, amino acids are grouped in one embodiment as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same group. Nonconservative substitutions constitute exchanging a member of one of these groups for a member of another.

Tables of conservative amino acid substitutions have been constructed and are known in the art. In other embodiments, examples of interchangeable amino acids include, but are not limited to the following: arginine and lysine; glutamate and aspartate; serine and threonine; glutamine and asparagine; and valine, leucine and isoleucine. In other embodiments, the following substitutions can be made: Ala (A) by leu, ile, or val; Arg (R) by gln, asn, or lys; Asn (N) by his, asp, lys, arg, or gln; Asp (D) by asn, or glu; Cys (C) by ala, or ser; Gln (Q) by glu, or asn; Glu (E) by gln, or asp; Gly (G) by ala; His (H)by asn, gln, lys,or arg; Ile (I) by val, met, ala, phe, or leu; Leu (L) by val, met, ala, phe, or ile; Lys (K) by gln, asn, or arg; Met (M) by phe, ile, or leu; Phe (F) by leu, val, ile, ala, or tyr; Pro (P) by ala; Ser (S) by thr; Thr (T) by ser; Trp (W) by phe, or tyr; Tyr (Y) by trp, phe, thr, or ser; and Val (V) by ile, leu, met, phe, or ala.

Other considerations for amino acid substitutions include whether or not the residue is located in the interior of a protein or is solvent—(i.e., externally) exposed. For interior residues, conservative substitutions include for example: Asp and Asn; Ser and Thr; Ser and Ala; Thr and Ala; Ala and Gly; Ile and Val; Val and Leu; Leu and Ile; Leu and Met; Phe and Tyr; and Tyr and Trp. For solvent-exposed residues, conservative substitutions include for example: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Be and Val; and Phe and Tyr.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally-occurring purine or pyrimidine base found in DNA (e.g., an adenine "A," a guanine "G," a thymine "T" or a cytosine "C") or RNA (e.g., an "A," a "G," a uracil "U" or a "C"). The term nucleobase also includes non-natural bases as described below. The term "nucleic acid" encompasses the terms "oligonucleotide" and "polynucleotide," each as a subgenus of the term "nucleic acid."

As used herein, the terms "complementary" or "complement" also refer to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

The term "homologous" or "% identity" as used herein means a nucleic acid (or fragment thereof), or a protein (or a fragment thereof) having a degree of homology to the corresponding natural reference nucleic acid, or protein, that is at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% identical thereto. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

Percentage sequence identities can be determined with protein sequences maximally aligned by the Kabat numbering convention. After alignment, if a particular polypeptide region is being compared with the same region of a reference polypepetide, the percentage sequence identity between the subject and reference polypeptide region is the number of positions occupied by the same amino acid in both the subject and reference polypeptide region divided by the total number of aligned positions of the two regions, with gaps not counted, multiplied by 100 to convert to percentage.

In one embodiment "% identity" represents the number of amino acids which are identical at corresponding positions in two sequences of a protein having the same or similar activity. For example, two amino acid sequences each having 100 residues will have at least 90% identity when 90 of the amino acids at corresponding positions are the same. Similarly, in one embodiment "% identity" represents the number of nucleotides which are identical at corresponding positions in two sequences of a nucleic acid encoding the same or similar polypeptides. For example, two nucleic acid sequences each having 100 nucleotides will have 90% identity when 90 of the nucleotides in homologous positions are the same.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Non-limiting applications include isolating a nucleic acid, such as a gene or a nucleic acid segment thereof, or detecting at least one specific mRNA transcript or a nucleic acid segment thereof, and the like. Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid, the length and nucleobase content of the target sequence, the charge composition of the nucleic acid, and to the presence or concentration of formamide, tetramethylammonium chloride or other solvent in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization to achieve varying degrees of selectivity of a nucleic acid towards a target sequence are used. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suit a particular application.

Herein certain embodiments, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

Where used herein in reference to a bacterium, the term "mutant" is intended to refer to a bacterium comprising a mutation in a "wild-type" or parental bacterium. "Wild-type" refers to the typical form (genotype and/or phenotype) of a bacterium, gene, nucleic acid, or protein as it occurs in nature and/or is the most common form in a natural population. In reference to a gene or nucleic acid, the term "mutation" refers to a gene or nucleic acid comprising an alteration in the wild type, such as but not limited to, a nucleotide deletion, insertion, and/or substitution. A mutation in a gene or nucleic acid generally results in either inactivation, decrease in expression or activity, increase in expression or activity, or another altered property of the gene or nucleic acid in the mutant bacterium comprising the mutation. In reference to a protein, the term "mutation" refers to protein comprising an alteration in the wild type, such as but not limited to, one or more amino acid deletions, insertions, and/or substitutions. A mutation in a protein generally results in either inactivation, decrease in activity or effect, increase in activity or effect, or another altered property or effect of the protein in the mutant bacterium comprising the mutation. A mutant bacterium may comprise a gene or nucleic acid comprising a mutation. A mutant bacterium may also comprise a deletion of one or more entire genes, the deletion of the one or more genes comprising the mutation in the mutant bacterium. A mutant bacterium may also comprise an insertion of one or more additional genes, the insertion of the one or more additional genes comprising the mutation in the mutant bacterium. The additional one or more genes may be duplicates of a native gene already present in the wild-type bacterium, or may be non-native genes. A mutant bacterium may also comprise a substitution of one or more native genes by one or more non-native genes or mutated genes, the substitution comprising the mutation in the mutant bacterium.

Where used herein, the terms "hyperporinated" or "hyperporination" or "pore-modified" refer to bacterial mutants comprising genes encoding modified protein nanopores, e.g., a genetically modified OrbA nanopore, that result in increased cell outer membrane permeability in the mutant bacteria.

Where used herein, the term "efflux-proficient" refers to bacteria which comprise non-modified efflux pumps that function in a manner equal to or similar to the wild type efflux pump.

Where used herein, the term "efflux-deficient" refers to bacterial mutants (e.g., AbΔ3, PΔ3, ΔTolC and BtΔ2) which comprise genes encoding modified efflux pumps that have impaired active efflux activity as compared to the efflux-proficient pump of the wild type.

The novel constructed bacterial mutants and strains of the present disclosure can be used for example in methods comprising, but not limited to: (i) high-throughput screening programs to identify compounds with anti-bacterial activities; (ii) counter-screens to separate contributions of active efflux and uptake to a given compound cell permeation and accumulation; (iii) lead development efforts to build structure-activity relationships separately for active efflux and uptake for a given compound; (iv) improvement of the intracellular compound accumulation without inhibiting efflux; and (v) improvement of the intracellular compound accumulation by bypassing efflux pumps.

The sensitization/permeabilization methods of the present disclosure can be applied to all Gram-negative bacteria containing a typical outer membrane composed of lipids, lipopolysaccharides and porins, including but not limited to those shown below in Table 1, which is a list of clinically important human pathogens that are most commonly targeted in current drug discovery programs.

TABLE 1. Examples of bacteria which can be modified according to the present disclosure.
1. *Escherichia coli* and other *Escherichia* species (spp)
2. *Klebsiella pneumoniae* and *Klebsiella* spp.
3. *Salmonella enterica* and *Salmonella* spp.
4. *Enterobacter cloacea* and *Enterobacter* spp.
5. *Burkholderia cenocepacia* complex
6. *Burkholderia thailandensis, Burkholderia cepacia,* and other *Burkholderia* spp.
7. *Acinetobacter baumannii*
8. *Pseudomonas aeruginosa* and *Pseudomonas* spp.
9. *Yersinia pestis* and *Y. pneumoniae*
10. *Shigella* spp.
11. *Francisella tularensis* and *Francisella* spp.
12. *Borrelia* spp.
13. *Niesseria meningitidis* and *N. gonorrhoeae*
14. *Serratia* spp.
15. *Proteus mirabilis* and *Proteus* spp.
16. *Haemophilus influenza* and *Haemophilus* spp.
17. *Vibrio cholera* and *Vibrio* spp.
18. *Citrobacter* spp.
19. *Bacteroides fragilis* and *Bacteroides* spp.

Several embodiments of the present disclosure, having now been generally described, will be more readily understood by reference to the following examples and embodiments, which are included merely for purposes of illustration, and are not intended to be limiting. The following detailed examples of the present disclosure are to be construed, as noted above, only as illustrative, and not as limitations of the embodiments described herein in any way whatsoever. Those skilled in the art will promptly recognize appropriate variations from the various compositions, structures, components, procedures and methods.

EXPERIMENTAL

Construction of Plasmids and Strains

Bacterial strains and plasmids used in this study are listed in Table 2.

TABLE 2

| Strains and Plasmids | | |
|---|---|---|
| | Relevant Genotype | Source |
| Strain | | |
| *P. aeruginosa* PAO1 | Wild type | O. Lomovskaya |
| GKCW111 | PAO1 attTn7::mini-Tn7T-Gm-lacI$^q$-pLAC-MCS | This study |
| GKCW119 | PAO1 attTn7::mini-Tn7T- Gm$^r$-lacI$^q$-pLAC-fhuAΔCΔ4L | This study |
| PAO1 (PaΔ3L) | PAO1 but ΔmexAB ΔmexCD ΔmexXY | O. Lomovskaya |
| GKCW112 | PAO1Δ3 attTn7::mini-Tn7T- Gm$^r$-lacI$^q$-pLAC-MCS | This study |

TABLE 2-continued

Strains and Plasmids

| | Relevant Genotype | Source |
|---|---|---|
| GKCW120 | PAO1Δ3 attTn7::mini-Tn7T- Gm$^r$-lacI$^q$-pLAC-fhuAΔCΔ4L | This study |
| *B. thailandensis* E264 | Wild type | H. Schweizer |
| Bt-RHA | E264 glmS1 attTn7::miniTn7-Tp-RHA | This study |
| Bt-RHA- BtPore | E264 glmS1 and glmS2 attTn7::miniTn7-Tp-RHA-orbA ((OrbA lacking the cork and four extracellular loops, and with C-terminal 10His tag). | This study |
| Bt38 (BtΔ2) | E264 ΔbpeAB-oprA::FRT ΔamrAB-oprA::FRT | H. Schweizer |
| BtΔ2-RHA | Bt38 glmS1 attTn7:: miniTn7-Tp-RHA | This study |
| BtΔ2-RHA-BtPore | Bt38 glmS1 and glmS2 attTn7::miniTn7-Tp-RHA-orbA | This study |
| *B. cepacia* 25416 | Wild type | ATCC |
| Bc-RHA | Bc attTn7::miniTn7-Tp-RHA | This study |
| Bc-RHA- BtPore | Bc attTn7::miniTn7-Tp-RHA-orbA (OrbA$_{ΔCork, Δ4Loop, 10His}$); expresses OrbA | This study |
| *A. baumanii* 17978 | Wild type | ATCC |
| JWW19 (Ab-ARA) | ATCC 17978 attTn7::miniTn7-Tp$^r$-araC-P$_{araBAD}$-MCS (pTJ1) | This study |
| JWW20 (Ab-ARA-EcPore) | ATCC 17978 attTn7::miniTn7-Tp$^r$-araC-P$_{araBAD}$-fhuA (FhuA$_{ΔCork, Δ4Loop, 6His}$) (pTJ1-FhuA) | This study |
| IL119 (AbΔ3) | ATCC 17978 ΔadeIJK::FRA ΔadeAB::FRT ΔadeFGH::FRT | This study |
| IL122 (AbΔ3-ARA) | ATCC 17978 Δ3 attTn7::miniTn7-Tp$^r$-araC-P$_{araBAD}$-MCS (pTJ1) | This study |
| IL123 (AbΔ3-ARA-EcPore) | ATCC 17978 Δ3 attTn7::miniTn7-Tp$^r$-araC-P$_{araBAD}$-fhuA(FhuA$_{ΔCorkΔ4Loop, 6His}$) (pTJ1-FhuA) | This study |
| Plasmids | | |
| pTNS3 [a, b] | Ap$^r$; Helper plasmid encoding Tn7 transposase proteins TnsABCD from P1 and P$_{lac}$ promoter | 1 |
| pUC18T-mini-Tn7T-LAC- (Gm$^r$) [a, b] | A suicide delivery vector | 1 |
| pUC18T-mini-Tn7T-araC-P$_{BAD}$-(Tp$^r$) [a, b] | A suicide delivery vector | 1 |
| pGK-LAC-FhuA ΔC/Δ4L (Gm$^r$) [a, b] | pUC18T mini-Tn7T- LAC- Gm$^r$-vector carrying fhuA ΔC/Δ4L gene | 4 |
| pDW- araC-P$_{araBAD}$-fhuA ΔC/Δ4L -(Tp$^r$) [a, b] | pUC18T mini-Tn7T- araC-P$_{BAD}$- Tp$^r$ vector carrying fhuA ΔC/Δ4L gene | 4 |
| pPR-IBA1- FhuA ΔC/Δ4L | pET-based plasmid containing fhuA ΔC/Δ4L gene | 2 |
| pUC18T-mini-Tn7-Tp-RHA [b] | Ap$^r$; Tp$^r$; miniTn7T cassette containing rhaRS-P$_{rhaBAD}$ | This study |
| pUC18T-mini-Tn7-Tp-RHA-orbA | pUC18T mini-Tn7T- LAC- Tp$^r$-vector carrying OrbA$_{ΔCork, Δ4Loop, 10His}$ from P$_{rhaBAD}$ | This study |
| pAT02 | pMMB67EH with Rec$_{Ab}$ system, Amp$^r$ | 3 |
| pAT03 | pMMB67EH with FLP recombinase, Amp$^r$ | 3 |
| pMo130-TelR [a] | Suicide plasmid, xylE$^+$, sacB$^+$, Km$^r$, Tel$^r$ | 5 |
| pIL117 | pMo130-Tel$^r$ plasmid containing gentamicin-resistance cassette, Gm$^r$ | This study |
| pIL118 | pMoTΔadeAB::Gm$^r$ containing 0.5 kb UP (adeA) and 0.5 kb DOWN (adeB) fragments; Tel$^r$, Gm$^r$ | This study |
| pIL119 | pMoTΔadeFGH::Gm$^r$ containing 0.5 kb UP (adeF) and 0.5 kb DOWN (adeH) fragments; Tel$^r$, Gm$^r$ | This study |
| pIL121 | pMoTΔadeIJK::Gm$^r$ containing 1 kb UP (adeI) and 1 kb DOWN (adeK) fragments; Tel$^r$, Gm$^r$ | This study |
| pEx18Ap | oriT$^+$ sacB$^+$ gene replacement vector with multiple-cloning site from pUC18; Amp$^r$ | H. Schweizer |
| pIL127 | pEx18Ap ΔadeIJK::Gm containing 1 kb UP (adeI) and 1 kb DOWN (adeK) fragments; Amp$^r$, Gm$^r$ | This study |
| pTJ1 [b] | Ap$^r$; Tp$^r$; miniTn7T cassette containing araC-P$_{araBAD}$ | 6 |

[a] Ap$^r$, Gm$^r$, Tel$^r$, Tp$^r$ genes encoding resistance to ampicillin, gentamicin, tellurite, and trimethoprim, respectively.

[b] P$_{lac}$, P$_{araBAD}$, P$_{TAC}$, P$_{rhaBAD}$, encode the *E. coli* lac, arabinose, lac/trp hybrid, and rhamnose promoters; P1 encodes the P1 integron promoter; P$_{S12}$ encodes the *B. thailandensis* ribosomal protein S12 promoter; PC$_{S12}$ encodes the *B. cenocepacia* rpsL promoter driving transcription of Tel$^r$ or Tp$^r$ genes; P$_λ$ encodes the λ repressor promoter.

[1] Choi K-H, Schweizer H P. 2006. mini-Tn7 insertion in bacteria with single attTn7 sites: example *Pseudomonas aeruginosa*. Nat Protocols 1: 153-161.

[2] Mohammad M M, Howard K R, Movileanu L. 2011. Redesign of a plugged beta-barrel membrane protein. J Biol Chem 286: 8000-13.

[3] Tucker A T, Nowicki E M, Boll J M, Knauf G A, Burdis N C, Trent M S, Davies B W. 2014. Defining Gene-Phenotype Relationships in *Acinetobacter baumannii* through One-Step Chromosomal Gene Inactivation. mBio 5.

[4] Krishnamoorthy G, Wollscheck D, Weeks J W, Croft C, Rybenkov V V, Zgurskaya H I. 2016. Breaking the Permeability Barrier of *Escherichia coli* by Controlled Hyperporination of the Outer Membrane. Antimicrob Agents Chemother 60: 7372-7381.

[5] Amin I M, Richmond G E, Sen P, Koh T H, Piddock L J, Chua K L. 2013. A method for generating marker-less gene deletions in multidrug-resistant *Acinetobacter baumannii*. BMC Microbiol 13: 158.

[6] Damron F H, McKenney E S, Barbier M, Liechti G W, Schweizer H P, Goldberg J B. 2013. Construction of mobilizable mini-Tn7 vectors for bioluminescent detection of gram-negative bacteria and single-copy promoter lux reporter analysis. Appl Environ Microbiol 79: 4149-53.

*P. aeruginosa* (Pae) Strains

To construct pGK-LAC-fhuA ΔC/Δ4L (Gm'), the gene encoding FhuA ΔC/Δ4L (EcPore) was amplified from the pPR-IBA1-FhuA ΔC/Δ4L plasmid. The PCR product was ligated with the pUC18-mini-Tn7T-LAC suicide delivery vector restricted with SacI and KpnI enzymes and transformed into *E. coli* DH5α competent cells and plated on LB agar plates containing Gentamycin (30 µg/ml). The colonies were screened for the insertion of FhuA ΔC/Δ4L gene into the vector by restriction digest analysis.

Insertion of mini-Tn7T-LAC-FhuA ΔC/Δ4L (Gm') onto the chromosome of *P. aeruginosa* PAO1 strain was achieved as described by Choi and Schweizer(1). Briefly, the suicide delivery vector carrying the fhuA ΔC/Δ4L gene and the helper plasmid pTNS3 were electroporated into PAO1 and PaΔ3 strains and grown for 1 h in LB medium containing 1 mM glucose. The cells were then plated onto LB agar containing gentamicin at 30 µg/ml (PAO1) or 15 µg/ml (PaΔ3) and incubated for 16 h at 37° C. Resulting colonies were selected and confirmed for the insertion by PCR using glmS down and glmS UP primers (see Table 3 in U.S. Provisional Patent Application Ser. No. 62/560,999).

*B. thailandesis* (Bt) and *B. cepacia* (Bc) Strains

The *B. thailandensis* orbA gene was modified to delete the coding sequence for the periplasmic cork domain and the four extracellular loops of OrbA protein. This synthetic (mutant) orbA (OrbA ΔC/Δ4L) gene was cloned into pUC57 between the SacI/HindIII sites. The DNA coding sequence (SEQ ID NO:1) for the OrbA mutant BtPore is shown in Table 3, this sequence includes the Thrombin cleavage site and a deca-histidine affinity tag. The amino acid sequence (SEQ ID NO:2) of the OrbA mutant BtPore protein is shown in Table 4. The mutant OrbA protein can be made without the Thrombin cleavage site or histidine affinity tag at the C-terminal end (e.g., see Table 5, SEQ ID NO:3), or with an alternate affinity tag which substitutes for the His tag of SEQ ID NO:2. A NcoI site was engineered to encode the Start Codon for cloning into pUC18T-mini-Tn7T-RHA, which encode optimized Shine-Dalgarno sequences in frame to their NcoI sites. To construct pUC18T-mini-Tn7T-Tp-RHA, the rhaRS-$P_{rhaBAD}$ promoter was amplified with primers RhaR NsiI REV and P-rhaBAD SpeI/NcoI REV (see Table 3 in U.S. Provisional Ser. No. 62/560,999). PCR product and pUC18T-miniTn7T-Tp were digested with NsiI/SpeI and ligated using T4 ligase, following manufacturer's protocols (NEB). The DNA sequence of the pUC18T-mini-Tn7-Tp-RHA-orbA plasmid encoding the BtPore protein is shown in Table 6 (SEQ ID NO:4). SEQ ID NO:4 includes the pUC18T-mini-Tn7-Tp core, a BtPore sequence, a Prha promoter for rhamnose-dependent expression of the BtPore sequence, and RhaR and RhaS sequences for rhamnose-dependent activation of the Prha promoter sequence. As noted, the BtPore-encoding plasmid could be constructed without a sequence for encoding an affinity tag in the BtPore protein.

Mini Tn7 cassettes were routinely integrated onto the chromosome of *B. thailandensis* or *B. cepacia* by tri-parental mating with recipient *B. thailandensis* or *B. cepacia* with the donors RHO3/pTNS3 and SM10λpir+ carrying pUC18T-based mini Tn7 cassettes. Mating was carried out by growing strains on LBA plates with appropriate selection markers. Overnight cultures were diluted, 1 to 100 for recipient and RHO3/pTNS3 or 1:20 for SM10λpir+ carrying pUC18T-based mini Tn7 cassettes, into fresh LB containing appropriate selection markers and grown at 37° C. to OD ~0.2. Cells were collected by centrifugation at 3220×g for 20 min and gently resuspended in LB to concentrate 100×. 10 μl of each strain was mixed in a sterile centrifuge tube and 10 μl of tri-parental mixture was spotted and allowed to adsorb onto a dried LBA plate containing 0.3 mM diamino palmitic acid. Mating reactions were incubated at 37° C. for 16 hours. Spots were scraped off the LBA plates and resuspended in 500 μl of LB. 100 μl of resuspended mating reaction was plated onto LBA containing 25 μg/ml polymyxin B and 100 μg/ml trimethoprim. Integrants were screened by stable growth on LBA plates containing 25 μg/ml polymyxin B and 100 μg/ml trimethoprim for Bt and 10 μg/ml polymyxin B and 10 μg/ml trimethoprim, pigment production on LBA for *B. cepacia*, as well as PCR confirmation of integration into either or both attTn7 sites at gimS1 or glmS2.

*A. baumannii* (Ab)

A suicide vector harboring a tellurite-resistance marker pMo130-$Tel^R$ was first created by inserting a gentamicin-resistance cassette to replace a kanamycin-resistance marker. To construct the suicide plasmid for deletion of efflux pumps, a 1 kb (for adeIJK) and 0.5 kb (for adeFGH and adeAB) DNA fragment located upstream and downstream of the efflux pump operons were amplified from genomic DNA. The constructed pIL118, pIL119 and pIL121 plasmids were used as templates to amplify ΔadeIJK::Gm, ΔadeFGH::Gm and ΔadeAB::Gm fragments, correspondingly.

The inactivation of adeIJK gene was done by cloning AadeIJK::Gm PCR product into pEX18Ap. The resulting plasmid construct pIL127 was first introduced into *E. coli* SM10λpir and subsequently delivered into *A. baumannii* by biparental conjugation. *A. baumannii* transconjugants (first crossovers) were selected on LB agar containing 30 μg/ml gentamicin and 100 μg/ml trimethoprim. During the second cross-over, mutants with gene deletion were selected for loss of sacB by passaging the first cross-over recombinants in LB agar containing 10% sucrose.

The inactivation of adeAB and adeFGH genes were done using RecAB as described in Nikaido H. 2003, Molecular basis of bacterial outer membrane permeability revisited. Microbiol Mol Biol Rev 67:593-656. We used electrocompetent cells at a density of $10^{10}$ CFU/reaction and 5 μg of PCR product with 0.5 kb of flanking homology. We obtained approximately 10-50 colonies from each transformation, depending on the gene being targeted for replacement. The gentamicin resistance cassette was removed by transformation of the pAT03 plasmid and activation of the FLP recombinase enzyme. Genomic deletions of the adeAB, adeFGH and adeIJK operons in the mutants were verified by comparing the PCR amplimers obtained from the wild type strain and corresponding pump gene deletion mutants.

Mini Tn7 cassettes were routinely integrated onto the chromosome of *A. baumannii* WT and AbΔ3 strains by tri-parental mating with recipient *A. baumannii*, RHO3/pTNS3, and SM10λpir+ carrying pTJ1 or pDW-araC-$P_{araBAD}$-fhuA ΔC/Δ4L (see Table 2). Mating was carried out by growing strains on LBA plates with appropriate selection markers. Overnight cultures were diluted, 1 to 100 for recipient and RHO3/pTNS3 or 1:20 for SM10λpir+ carrying pDW-araC-$P_{araBAD}$-fhuA ΔC/Δ4L, into fresh LB containing appropriate selection markers and grown at 37° C. to OD ~0.5. Cells were collected by centrifugation at 4000×g for 20 min and gently resuspended in LB to concentrate 100×. 10 μl of each strain was mixed in a sterile centrifuge tube and 10 μl of tri-parental mixture was spotted and allowed to adsorb onto a dried LBA plate containing 0.3 mM diaminopimelic acid. Mating reactions were incubated at 37° C. for 16 hours. Spots were scraped off the LBA plates and resuspended in 500 µl of LB. 100 µl of resuspended mating reaction was plated onto LBA containing 100 µg/ml streptomycin and 100 µg/ml trimethoprim. Integrants were screened by stable growth on LBA plates containing 100 µg/ml streptomycin and 100 µg/ml trimethoprim. Resulting colonies were selected and confirmed for the insertion of EcPore by PCR. We also found that pTJ1-based plasmids used for the chromosomal integration in this and previous studies can self-replicate in this Abau strain (data not shown). This plasmid is also the reason for the β-lactam resistance of the constructed Abau strains (see Table 9). Primers used in the construction of plasmids are listed in Table 3 in U. S. Provisional Ser. No. 62/560,999.

Experimental Conditions

Luria-Bertani (LB) broth (10 g of Bacto tryptone, 5 g of yeast extract, and 5 g of NaCl per liter, pH 7.0) or LB agar (LB broth with 15 g of agar per liter) were used for bacterial growth. When indicated, cultures were induced with 0.1 mM isopropyl β-D-1-thiogalactopyranoside (IPTG), 1% L-arabinose, or 0.2% L-rhamnose to induce expression of "Pore" proteins. For selection, gentamicin (*P. aeruginosa*-30 µg/ml or 15 µg/ml, *A. baumannii* 30 µg/ml), trimethoprim (*B. thailandensis, B. cepacia, E. coli* and *A. baumannii* 100 µg/ml), tellurite (*E. coli* 10 µg/ml), ampicillin (100 µg/ml), carbenicillin (200 µg/ml), streptomycin (100 µg/ml) and polymyxin B (10 µg/ml or 25 µg/ml) were used. Susceptibility to different classes of antibiotics were determined by two-fold broth dilution method. (Krishnamoorthy et al., 2016, op cit.)

Uptake assay was performed in a temperature controlled micro-plate reader (TECAN SPARK 10 M multimode microplate reader) equipped with a sample injector, in fluorescence mode.(24) Cells from frozen stocks were inoculated into LB medium incubated for 16 h at 37° C. Cells were then sub-cultured into fresh 30 ml of LB medium and grown at 37° C. up to $OD_{600}$-0.3. The cells were then induced with 0.1 mM IPTG or 0.2% rhamnose or 1% arabinose and grown until $OD_{600}$ is 1.0, collected by centrifugation at 4,000 rpm for 40 min at room temperature and washed in 25 ml HEPES-KOH buffer 50 mM (pH 7.0) containing 1 mM magnesium sulfate and 0.4 mM glucose (HMG buffer). The cells in HMG buffer were adjusted to OD~1.0 and kept at room temperature during the experiment. Fluorescence intensities from HT and NPN uptake experiments were plotted against time in Microsoft Excel and normalized to the emission before cells were added. The data was imported into MATLAB (MathWorks) to be fitted to a simple exponential equation in the form of $F=A_1+A_2(1-\exp(-kt))$.

For protein analyses, membrane fractions were isolated from Pae or Bt or Bc cells by ultracentrifugation. Outer membrane fractions were enriched by solubilization of inner membrane proteins in buffer containing 50 mM Tris-HCl (pH 8.0), 150 mM NaCl, 1 mM PMSF, and 0.2% Triton X-100 and separated from the insoluble outer membrane fractions by ultracentrifugation. The resulting pellet was further solubilized in 50 mM Tris-HCl (pH 8.0), 150 mM NaCl, 1 mM PMSF, and 5.0% Triton X-100 followed by ultracentrifugation to remove insoluble components. The supernatant was incubated with His•Bind Resin (Novagen), which was previously charged with 50 mM $CuSO_4$. The pore protein was eluted with 20 mM Tris-HCl (pH 8.0), 500 mM NaCl, 1 mM PMSF, 0.2% Triton X-100, and 400 mM imidazole. The eluted fractions were analyzed by 12% SDS-PAGE followed by immunoblotting with primary monoclonal anti-Histidine tag antibodies (Thermofisher Inc.) and a secondary alkaline phosphatase-conjugated antimouse antibody (Sigma). The 5-bromo4-chloro-3-indoyl phosphate (BCIP) and nitroblue tetrazolium (NBT) substrates were used to visualize the bands. The pore was quantified using the Quantity One software (Bio-Rad) with a His tagged *P. aeruginosa* protein TriC as a standard.

Hierarchical clustering was done using Matlab Statistics toolbox using unweighted average euclidean distances between logarithms of measured MIC ratios. Principle component analysis (PCA) revealed that the first two components describe the effect of hyperporination and active efflux and are responsible for 77% of the overall variance, 93% for four components (Table 10). The coordinates of the PCA vectors are shown in Table 10 together with the percent explained variance for each vector. The R-squared index analysis suggested the existence of three clusters in the distribution. PCA coordinates were then fit to a Gaussian mixture model using expectation maximization (EM) algorithm. Both the hierarchical and EM algorithms produced the same separation of data into clusters, which did not change upon the removal of up to 20% of constituent points from each cluster.

TABLE 3

BtPore DNA coding sequence (SEQ ID NO: 1)

| | |
|---|---|
| 3845 | ATGGAG TGGGCAACCA GCACGCGCGT GCGTGCGATC GCGGCGGCGG CAGGCGTGGC |
| 3901 | GTTCTGCGCG GCGGCGAGTC ATGCGCAGGC ACAGGCGATT CGCGAGGTCG GCGTGCAGGT |
| 3961 | GGGCAACTAC GCGCGCAAGC AGCTGATGTT CGATATCGGC GACAAGATCG ACAAGGATGG |
| 4021 | CACGCTGTCG TACCGGATCG TCGGCGTCGG CCGCGACGGC AACGCGCAGA CGGGGCCGCT |
| 4081 | CGCCGACCAG CGCGTGTCGT TCGCGCCGTC GCTCAAGTGG CAGCCGAACG CAAACACGTC |
| 4141 | GCTCACGCTC GCCGCGACGT ACCTGCAGGA CTGGGGCGAC ACGGGCAACA GCGAGGGCAG |
| 4201 | CCACTACCGC AAGAAGCAAT GGTCGATCGG CTATCAGTTC GAGCACAAGC TGAACCCGGT |
| 4261 | GTGGACGTTC CGGCAGAACG TGCGCTGGAT GCACCTGGCG CTCGACGACG CGTCCGTCTA |
| 4321 | CGGCAACAGC GAGGGCAGCA CGCGCTACGC GGGCCTGTTC CAGTTCAACT ACAGCCGCTT |
| 4381 | CGACGTCGAC AACCAGGCGC AGGCGAAATT CACGACAGGC CCGTTGAGCC ACACACTGCT |
| 4441 | GTTCGGCTTC GACTACAACC GGCAGACGAC GACCGACAGC GAATGGCTCG CGGGCAACAG |

TABLE 3-continued

| BtPore DNA coding sequence (SEQ ID NO: 1) | |
|---|---|
| 4501 | CGAGGGCAGC GCGTACCCGC GCACCGACAC GAAGACGACG CTCAACGCCT TCGGCCTGTA |
| 4561 | CGTGCAGGAC CAGATCAAGT GGCAGCGCTG GGTGCTCACG CTCGGCGGCC GGCAGGACTG |
| 4621 | GACGCGCACG TCGCAGGACG ACATCGCGAA CTCGGCGAGC TTCAAGCAGA ACGACCACGC |
| 4681 | GTTCAGCGGG CGCGTCGGCC TGACCTATCT CGGCGATTAC GGCCTCGCGC CGTACCTCAG |
| 4741 | CTATTCGACG TCGTTCAATC CGCAGATCGG CGTGGGCGGC GGGCGCCAGA TCGAGGCTGG |
| 4801 | CCTGCGCTGG CAGCCGCCGG GCAAGAACCT GATGCTGAAC GCGGCCGTCT ACCAGATCAA |
| 4861 | CCAGACGAAC GTCGCGATGA GCAATCCGAA CGATCCGACG AGCAGCACGT TCGTGCAGGT |
| 4921 | GGGCGAGGTG CGCTCGCGCG GCGTCGAGCT GAGCGCGGTG GGCAACCTGT CGCGCGAGCT |
| 4981 | GTCGGTGATC GCCGCGTACG TCTATCAGGA CGTGAAGAAC GTGCAGGCGA ATGACAACAC |
| 5041 | GCTGAACAAG TGGCCCGTCG ACGTGCCGCG CCCGCGCCAG ATCGCGTCGC TGTGGGCCGA |
| 5101 | CTGGACGTGG CGCAACGGGC CGCTCACGGG CTTCGGCGTC GGCGCCGGCG TGCGCTACAT |
| 5161 | GGGCAACAGC GAGGGCAGCA GCTACACGCT GTTCGACGCG GCGCTGCACT ACGAGCTGCG |
| 5221 | CAACTGGCGC TTCGCGCTCA ATGCGACGAA CCTGGGCAAC AGCGAGGGCA GCCGCACCGT |
| 5281 | GATCGCGACG GCGAAATACA ACTGGCTGGT GCCGCGCGGC AGCCACCACC ATCACCACCA |
| 5341 | TCACCACCAT CACTGA |

TABLE 4

| Amino acid sequence of BtPore protein with His affinity tag (SEQ ID NO: 2) |
|---|
| MEWATSTRVRAIAAAAGVAFCAAASHAQAQAIREVGVQVGNYARKQLMFD<br>IGDKIDKDGTLSYRIVGVGRDGNAQTGPLADQRVSFAPSLKWQPNANTSL<br>TLAATYLQDWGDTGNSEGSHYRKKQWSIGYQFEHKLNPVWTFRQNVRWMH<br>LALDDASVYGNSEGSTRYAGLFQFNYSRFDVDNQAQAKFTTGPLSHTLLF<br>GFDYNRQTTTDSEWLAGNSEGSAYPRTDTKTTLNAFGLYVQDQIKWQRWV<br>LTLGGRQDWTRTSQDDIANSASFKQNDHAFSGRVGLTYLGDYGLAPYLSY<br>STSFNPQIGVGGGRQIEAGLRWQPPGKNLMLNAAVYQINQTNVAMSNPND<br>PTSSTFVQVGEVRSRGVELSAVGNLSRELSVIAAYVYQDVKNVQANDNTL<br>NKWPVDVPRPRQIASLWADWTWRNGPLTGFGVGAGVRYMGNSEGSSYTLF<br>DAALHYELRNWRFALNATNLGNSEGSRTVIATAKYNWLVPRGSHHHHHHH<br>HHHStop |

TABLE 5

| Amino acid sequence of BtPore protein without Thrombin cleavage site and affinity tag (SEQ ID NO: 3) |
|---|
| MEWATSTRVRAIAAAAGVAFCAAASHAQAQAIREVGVQVGNYARKQLMFD<br>IGDKIDKDGTLSYRIVGVGRDGNAQTGPLADQRVSFAPSLKWQPNANTSL<br>TLAATYLQDWGDTGNSEGSHYRKKQWSIGYQFEHKLNPVWTFRQNVRWMH<br>LALDDASVYGNSEGSTRYAGLFQFNYSRFDVDNQAQAKFTTGPLSHTLLF<br>GFDYNRQTTTDSEWLAGNSEGSAYPRTDTKTTLNAFGLYVQDQIKWQRWV<br>LTLGGRQDWTRTSQDDIANSASFKQNDHAFSGRVGLTYLGDYGLAPYLSY<br>STSFNPQIGVGGGRQIEAGLRWQPPGKNLMLNAAVYQINQTNVAMSNPND<br>PTSSTFVQVGEVRSRGVELSAVGNLSRELSVIAAYVYQDVKNVQANDNTL<br>NKWPVDVPRPRQIASLWADWTWRNGPLTGFGVGAGVRYMGNSEGSSYTLF<br>DAALHYELRNWRFALNATNLGNSEGSRTVIATAKYNW |

TABLE 6

| DNA sequence of pUC18T-miniTn7T-TP-RHA-BtPore plasmid (SEQ ID NO: 4) | |
|---|---|
| pUC18T-miniTn7T-TP→ | |
| 1 | TCGCGCGTTT CGGTGATGAC GGTGAAAACC TCTGACACAT GCAGCTCCCG GAGACGGTCA |
| 61 | CAGCTTGTCT GTAAGCGGAT GCCGGGAGCA GACAAGCCCG TCAGGGCGCG TCAGCGGGTG |
| 121 | TTGGCGGGTG TCGGGGCTGG CTTAACTATG CGGCATCAGA GCAGATTGTA CTGAGAGTGC |
| 181 | ACCATATGCG GTGTGAAATA CCGCACAGAT GCGTAAGGAG AAAATACCGC ATCAGGCGCC |
| 241 | ATTCGCCATT CAGGCTGCGC AACTGTTGGG AAGGGCGATC GGTGCGGGCC TCTTCGCTAT |
| 301 | TACGCCAGCT AGAGGACCAG CCGCGTAACC TGGCAAAATC GGTTACGGTT GAGTAATAAA |
| 361 | TGGATGCCCT GCGTAAGCGG GTGTGGGCGG ACAATAAAGT CTTAAACTGA ACAAAATAGA |
| 421 | TCTAAACTAT GACAATAAAG TCTTAAACTA GACAGAATAG TTGTAAACTG AAATCAGTCC |
| 481 | AGTTATGCTG TGAAAAAGCA TACTGGACTT TTGTTATGGC TAAAGCAAAC TCTTCATTTT |
| 541 | CTGAAGTGCA AATTGCCCGT CGTATTAAAG AGGGGCGTGG GGTTCGAGGT CGACGGTATC |
| 601 | GATAAGCTAG CTTAATTAGC TGAGCTTGGA CTCCTGTTGA TAGATCCAGT AATGACCTCA |

TABLE 6-continued

| DNA sequence of pUC18T-miniTn7T-TP-RHA-BtPore plasmid (SEQ ID NO: 4) |
|---|

```
 661    GAACTCCATC TGGATTTGTT CAGAACGCTC GGTTGCCGCC GGGCGTTTTT TATTGGTGAG
 721    AATCCAAGCT AGACTGCGAT GAGTGGCAGG GCGGGGCGTA ATTTTTTAA GGCAGTTATT
 781    GGTGCCCTTA AACGCCTGGG GTAATGACTC TCTAGCTTGA GGCATCAAAT AAAACGAAAG
 841    GCTCAGTCGA AGACTGGGC CTTTCGTTTT ATCTGTTGTT TGTCGGTGAA CGCTCTCCTG
 901    AGTAGGACAA ATCCGCCGCT AGGAGCTTGC GGCCCGGACG ATGAGCTCGA ATTGGGGATC
 961    TTGAAGTACC TATTCCGAAG TTCCTATTCT CTAGAAAGTA TAGGAACTTC AGAGCGCTTT
1021    TGAAGCTGAT GTGCTTAAAA ACTTACTCAA TGGAATAATT CTAGATAATT CTTAGGCCAC
1081    ACGTTCAAGT GCAGCCACAG GATAAATTTG CACTGAGCCT GGGTGGGATT CGGACTCGAC
1141    CGCATAGCCT TCAGGAGTGA GTTTTGTGCA ATACCAACCG ACGACTTGAC CCTGCCAAGC
1201    GGCACCAGAT TTCTTGCGTA CGCGATCCCC TAAGCCAAAG GTGGCACTCA GGGGAAGCGC
1261    AAACTGCCCT GCAACGGGAG CGTTGGCTTC ATCGCTACTT TGACCCATGT CGAATCCTTC
1321    TTGTGAATCT ATTATGGCGA CAAGCAAATC GAGCTCTGAC TGCCTACCCC ACAACAACTA
1381    TCAGAAAGCA CCAGCACAAC GGCTGCCTAA CTTTGTTTTA GGGCGACTGC CCTGCTGCGT
1441    AACATCGTTG CTGCTCCATA ACATCAAACA TCGACCCACG GCGTAACGCG CTTGCTGCTT
1501    GGATGCCCGA GGCTAGACTG TACAAAAAAA CAGTCATAAC AAGCCATGAA AACCGCCACT
1561    GCGCCGTTAC CACCGCTGCG TTCGGTCAAG GTTCTGGACC AGTTGCGTGA GCGCATACGC
1621    TACTTGCATT ACAGTTTACG AACCGAACAG GCTTATGTCA ACTGGGTTCG TGAATTATCC
1681    ATTGCTGTTG ACAAAGGGAA TCAGGGGATC TTGAAGTTCC TATTCCGAAG TTCCTATTCT
1741    CTAGAAAGTA TAGGAACTTC AGAGCGCTTT TGAAGCTAAT TCGAGCTCGA TCATGCAT
```
←pUC18T-miniTn7T-TP RhaR→ TT
```
1801    AATCTTTCTG CGAATTGAGA TGACGCCACT GGCTGGGCGT CATCCCGGTT TCCCGGGTAA
1861    ACACCACCGA AAAATAGTTA CTATCTTCAA AGCCACATTC GGTCGAAATA TCACTGATTA
1921    ACAGGCGGCT ATGCTGGAGA AGATATTGCG CATGACACAC TCTGACCTGT CGCAGATATT
1981    GATTGATGGT CATTCCAGTC TGCTGGCGAA ATTGCTGACG CAAAACGCGC TCACTGCACG
2041    ATGCCTCATC ACAAAATTTA TCCAGCGCAA AGGGACTTTT CAGGCTAGCC GCCAGCCGGG
2101    TAATCAGCTT ATCCAGCAAC GTTTCGCTGG ATGTTGGCGG CAACGAATCA CTGGTGTAAC
2161    GATGGCGATT CAGCAACATC ACCAACTGCC CGAACAGCAA CTCAGCCATT TCGTTAGCAA
2221    ACGGCACATG CTGACTACTT TCATGCTCAA GCTGACCGAT AACCTGCCGC GCCTGCGCCA
2281    TCCCCATGCT ACCTAAGCGC CAGTGTGGTT GCCCTGCGCT GGCGTTAAAT CCCGGAATCG
2341    CCCCCTGCCA GTCAAGATTC AGCTTCAGAC GCTCCGGGCA ATAAATAATA TTCTGCAAAA
2401    CCAGATCGTT AACGGAAGCG TAGGAGTGTT TATCGTCAGC ATGAATGTAA AGAGATCGC
2461    CACGGGTAAT GCGATAAGGG CGATCGTTGA GTACATGCAG GCCATTACCG CGCCAGACAA
2521    TCACCAGCTC ACAAAAATCA TGTGTATGTT CAGCAAAGAC ATCTTGCGGA TAACGGTCAG
2581    CCACAGCGAC TGCCTGCTGG TCGCTGGCAA AAAAATCATC TTTGAGAAGT TTTAACTGAT
2641    GCGCCAC    ←RhaR
        CGT GGCTACCTCG GCCAGAGAAC GAAGTTGATT ATTCGCAATA TGGCGTACAA
2701    ATACGTTGAG AAGATTCGCG
```
RhaS→ TTATTGCAGA AAGCCATCCC GTCCCTGGCG AATATCACGC
```
2761    GGTGACCAGT TAAACTCTCG GCGAAAAAGC GTCGAAAAGT GGTTACTGTC GCTGAATCCA
```

TABLE 6-continued

DNA sequence of pUC18T-miniTn7T-TP-RHA-BtPore plasmid (SEQ ID NO: 4)

```
2821    CAGCGATAGG CGATGTCAGT AACGCTGGCC TCGCTGTGGC GTAGCAGATG TCGGGCTTTC

2881    ATCAGTCGCA GGCGGTTCAG GTATCGCTGA GGCGTCAGTC CCGTTTGCTG CTTAAGCTGC

2941    CGATGTAGCG TACGCAGTGA AAGAGAAAAT TGATCCGCCA CGGCATCCCA ATTCACCTCA

3001    TCGGCAAAAT GGTCCTCCAG CCAGGCCAGA AGCAAGTTGA CACGTGATGC GCTGTTTTCC

3061    AGGTTCTCCT GCAAACTGCT TTTACGCAGC AAGAGCAGTA ATTGCATAAA CAAGATCTCG

3121    CGACTGGCGG TCGAGGGTAA ATCATTTTCC CCTTCCTGCT GTTCCATCTG TGCAACCAGC

3181    TGTCGCACCT GCTGCAATAC GCTGTGGTTA ACGCGCCAGT GAGACGGATA CTGCCCATCC

3241    AGCTCTTGTG GCAGCAACTG ATTCAGCCCG GCGAGAAACT GAAATCGATC CGGCGAGCGA

3301    TACAGCACAT TGGTCAGACA CAGATTATCG GTATGTTCAT ACAGATGCCG ATCATGATCG

3361    CGTACGAAAC AGACCGTGCC ACCGGTGATG GTATAGGGCT GCCCATTAAA CACATGAATA

3421    CCCGTGCCAT GTTCGACAAT CACAATTTCA TGAAAATCAT GATGATGTTC AGGAAAATCC

3481    GCCTGCGGGA GCCGGGGTTC TATCGCCACG GACGCGTTAC CAGACGGAAA AAAATCCACA

3541    CTATGTAATA CGGTCAT ←RhaS

Prha→ ACT GGCCTCCTGA TGTCGTCAAC ACGGCGAAAT AGTAATCACG
3601    AGGTCAGGTT CTTACCTTAA ATTTTCGACG GAAAACCACG TAAAAAACGT CGATTTTTCA

3661    AGATACAGCG TGAATTTTCA GGAAATGCGG TGAGCATCAC ATCACCACAA TTCAGCAAAT

3721    TGTGAACATC ATCACGTTCA TCTTTCCCTG GTTGCCAATG GCCCATTTTC CTGTCAGTAA

3781    CGAGAAGGTC GCGAATTCAG GCGCTTTTTA GACTGGTCGT AATGAAATTC AGCAGGATCA

3841    CACC ←Prha

BtPore→
        ATGGAG TGGGCAACCA GCACGCGCGT GCGTGCGATC GCGGCGGCGG CAGGCGTGGC

3901    GTTCTGCGCG GCGGCGAGTC ATGCGCAGGC ACAGGCGATT CGCGAGGTCG GCGTGCAGGT

3961    GGGCAACTAC GCGCGCAAGC AGCTGATGTT CGATATCGGC GACAAGATCG ACAAGGATGG

4021    CACGCTGTCG TACCGGATCG TCGGCGTCGG CCGCGACGGC AACGCGCAGA CGGGGCCGCT

4081    CGCCGACCAG CGCGTGTCGT TCGCGCCGTC GCTCAAGTGG CAGCCGAACG CAAACACGTC

4141    GCTCACGCTC GCCGCGACGT ACCTGCAGGA CTGGGGCGAC ACGGGCAACA GCGAGGGCAG

4201    CCACTACCGC AAGAAGCAAT GGTCGATCGG CTATCAGTTC GAGCACAAGC TGAACCCGGT

4261    GTGGACGTTC CGGCAGAACG TGCGCTGGAT GCACCTGGCG CTCGACGACG CGTCCGTCTA

4321    CGGCAACAGC GAGGGCAGCA CGCGCTACGC GGGCCTGTTC CAGTTCAACT ACAGCCGCTT

4381    CGACGTCGAC AACCAGGCGC AGGCGAAATT CACGCACAGG CCGTTGAGCC ACACACTGCT

4441    GTTCGGCTTC GACTACAACC GGCAGACGAC GACCGACAGC GAATGGCTCG CGGGCAACAG

4501    CGAGGGCAGC GCGTACCCGC GCACCGACAC GAAGACGACG CTCAACGCCT TCGGCCTGTA

4561    CGTGCAGGAC CAGATCAAGT GGCAGCGCTG GGTGCTCACG CTCGGCGGCC GGCAGGACTG

4621    GACGCGCACG TCGCAGGACG ACATCGCGAA CTCGGCGAGC TTCAAGCAGA ACGACCACGC

4681    GTTCAGCGGG CGCGTCGGCC TGACCTATCT CGGCGATTAC GGCCTCGCGC CGTACCTCAG

4741    CTATTCGACG TCGTTCAATC CGCAGATCGG CGTGGGCGGC GGGCGCCAGA TCGAGGCTGG

4801    CCTGCGCTGG CAGCCGCCGG GCAAGAACCT GATGCTGAAC GCGGCCGTCT ACCAGATCAA

4861    CCAGACGAAC GTCGCGATGA GCAATCCGAA CGATCCGACG AGCAGCACGT TCGTGCAGGT

4921    GGGCGAGGTG CGCTCGCGCG GCGTCGAGCT GAGCGCGGTG GGCAACCTGT CGCGCGAGCT

4981    GTCGGTGATC GCCGCGTACG TCTATCAGGA CGTGAAGAAC GTGCAGGCGA ATGACAACAC
```

TABLE 6-continued

DNA sequence of pUC18T-miniTn7T-TP-RHA-BtPore plasmid (SEQ ID NO: 4)

```
5041    GCTGAACAAG TGGCCCGTCG ACGTGCCGCG CCCGCGCCAG ATCGCGTCGC TGTGGGCCGA

5101    CTGGACGTGG CGCAACGGGC CGCTCACGGG CTTCGGCGTC GGCGCCGGCG TGCGCTACAT

5161    GGGCAACAGC GAGGGCAGCA GCTACACGCT GTTCGACGCG GCGCTGCACT ACGAGCTGCG

5221    CAACTGGCGC TTCGCGCTCA ATGCGACGAA CCTGGGCAAC AGCGAGGGCA GCCGCACCGT

5281    GATCGCGACG GCGAAATACA ACTGGCTGGT GCCGCGCGGC AGCCACCACC ATCACCACCA

5341    TCACCACCAT CACTGA ←BtPore pUC18T-miniTn7T-TP→
        AGCT TGGGCCCGGT ACCTCGCGAA GGCCTTGCAG GCCAACCAGA

5401    TAAGTGAAAT CTAGTTCCAA ACTATTTTGT CATTTTTAAT TTTCGTATTA GCTTACGACG

5461    CTACACCCAG TTCCCATCTA TTTTGTCACT CTTCCCTAAA TAATCCTTAA AAACTCCATT

5521    TCCACCCCTC CCAGTTCCCA ACTATTTTGT CCGCCCACAG CGGGGCATTT TTCTTCCTGT

5581    TATGTTTGGG CGCTGCATTA ATGAATCGGC CAACGCGCGG GGAGAGGCGG TTTGCGTATT

5641    GGGCGCTCTT CCGCTTCCTC GCTCACTGAC CCGCTGCGCT CGGTCGTTCG GCTGCGGCGA

5701    GCGGTATCAG AGCTTATCGG CCAGCCTCGC AGAGCAGGAT TCCCGTTGAG CACCGCCAGG

5761    TGCGAATAAG GACAGTGAA GAAGGAACAC CCGCTCGCGG GTGGGCCTAC TTCACCTATC

5821    CTGCCCGGCT GACGCCGTTG GATACACCAA GGAAAGTCTA CACGAACCCT TTGGCAAAAT

5881    CCTGTATATC GTGCGAAAAA GGATGGATAT ACCGAAAAAA TCGCTATAAT GACCCCGAAG

5941    CAGGGTTATG CAGCGGAAAG TATACCTTAA GGATCCCCT GATAACGCAG AAAGAACAT

6001    GTGAGCAAAA GGCCAGCAAA AGGCCAGGAA CCGTAAAAAG GCCGCGTTGC TGGCGTTTTT

6061    CCATAGGCTC CGCCCCCCTG ACGAGCATCA CAAAAATCGA CGCTCGAGTC AGAGGTGGCG

6121    AAACCCGACA GGACTATAAA GATACCAGGC GTTTCCCCCT GGAAGCTCCC TCGTGCGCTC

6181    TCCTGTTCCG ACCCTGCCGC TTACCGGATA CCTGTCCGCC TTTCTCCCTT CGGGAAGCGT

6241    GGCGCTTTCT CATAGCTCAC GCTGTAGGTA TCTCAGTTCG GTGTAGGTCA TTCGCTCCAA

6301    GCTGGGCTGT GTGCACGAAC CCCCCGTTCA GCCCGACCGC TGCGCCTTAT CCGGTAACTA

6361    TCGTCTTGAG TCCAACCCGG TAAGACACGA CTTATCGCCA CTGGCAGCAG CCACTGGTAA

6421    CAGGATTAGC AGAGCGAGGT ATGTAGGCGG TGCTACAGAG TTCTTGAAGT GGTGGCCTAA

6481    CTACGGCTAC ACTAGAAGGA CAGTATTTGG TATCTGCGCT CTGCTGAAGC CAGTTACCTT

6541    CGGAAAAAGA GTTGGTAGCT CTTGATCCGG CAAACAAACC ACCGCTGGTA GCGGTGGTTT

6601    TTTTGTTTGC AAGCAGCAGA TTACGCGCAG AAAAAAAGGA TCTCAAGAAG ATCCTTTGAT

6661    CTTTTCTACG GGGTCTGACG CTCAGTGGAA CGAAAACTCA CGTTAAGGGA TTTTGGTCAT

6721    GAGATTATCA AAAAGGATCT TCACCTAGAT CCTTTTAAAT TAAAAATGAA GTTTTAAATC

6781    AATCTAAAGT ATATATGAGT AAACTTGGTC TGACAGTTAC CAATGCTTAA TCAGTGAGGC

6841    ACCTATCTCA GCGATCTGTC TATTTCGTTC ATCCATAGTT GCCTGACTCC CCGTCGTGTA

6901    GATAACTACG ATACGGGAGG GCTTACCATC TGGCCCCAGT GCTGCAATGA TACCGCGAGA

6961    CCCACGCTCA CCGGCTCCAG ATTTATCAGC AATAAACCAG CCAGCCGGAA GGGCCGAGCG

7021    CAGAAGTGGT CCTGCAACTT TATCCGCCTC CATCCAGTCT ATTAATTGTT GCCGGGAAGC

7081    TAGAGTAAGT AGTTCGCCAG TTAATAGTTT GCGCAACGTT GTTGCCATTG CTACAGGCAT

7141    CGTGGTGTCA CGCTCGTCGT TTGGTATGGC TTCATTCAGC TCCGGTTCCC AACGATCAAG

7201    GCGAGTTACA TGATCCCCCA TGTTGTGCAA AAAAGCGGTT AGCTCCTTCG GTCCTCCGAT
```

TABLE 6-continued

DNA sequence of pUC18T-miniTn7T-TP-RHA-BtPore plasmid (SEQ ID NO: 4)

```
7261    CGTTGTCAGA AGTAAGTTGG CCGCAGTGTT ATCACTCATG GTTATGGCAG CACTGCATAA

7321    TTCTCTTACT GTCATGCCAT CCGTAAGATG CTTTTCTGTG ACTGGTGAGT ACTCAACCAA

7381    GTCATTCTGA GAATAGTGTA TGCGGCGACC GAGTTGCTCT TGCCCGGCGT CAATACGGGA

7441    TAATACCGCG CCACATAGCA GAACTTTAAA AGTGCTCATC ATTGGAAAAC GTTCTTCGGG

7501    GCGAAAACTC TCAAGGATCT TACCGCTGTT GAGATCCAGT TCGATGTAAC CCACTCGTGC

7561    ACCCAACTGA TCTTCAGCAT CTTTTACTTT CACCAGCGTT TCTGGGTGAG CAAAAACAGG

7621    AAGGCAAAAT GCCGCAAAAA AGGGAATAAG GGCGACACGG AAATGTTGAA TACTCATACT

7681    CTTCCTTTTT CAATATTATT GAAGCATTTA TCAGGGTTAT TGTCTCATGA GCGGATACAT

7741    ATTTGAATGT ATTTAGAAAA ATAAACAAAT AGGGGTTCCG CGCACATTTC CCCGAAAAGT

7801    GCCACCTGAC GTCTAAGAAA CCATTATTAT CATGACATTA ACCTATAAAA ATAGGCGTAT

7861    CACGAGGCCC TTTCGTC ←pUC18T-miniTn7T-TP
```

Results

Hyperporination of the outer membrane is well tolerated by various species.

Figure 1B:
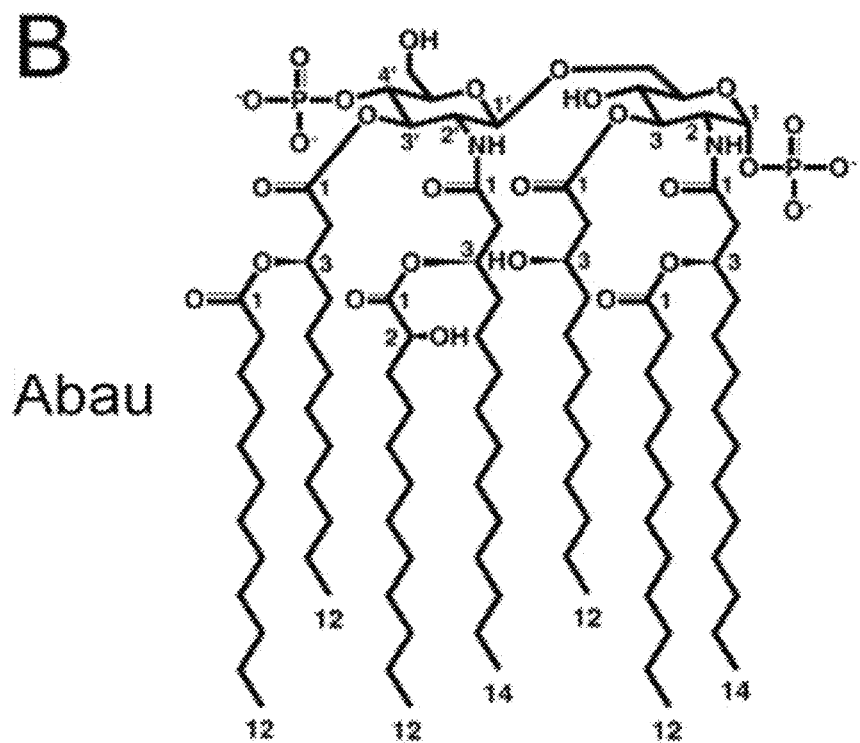
FIG. 1B shows structures of lipid A moieties and hyperporination of the outer membrane of a *A. baumannii* mutant constructed in accordance with the present disclosure. The immunoblotting analyses with a monoclonal anti-His antibody, the copy number of the expressed hyperpores per cell, and MICs of vancomycin (VAN) in the induced cells are shown.
Figure 1B:
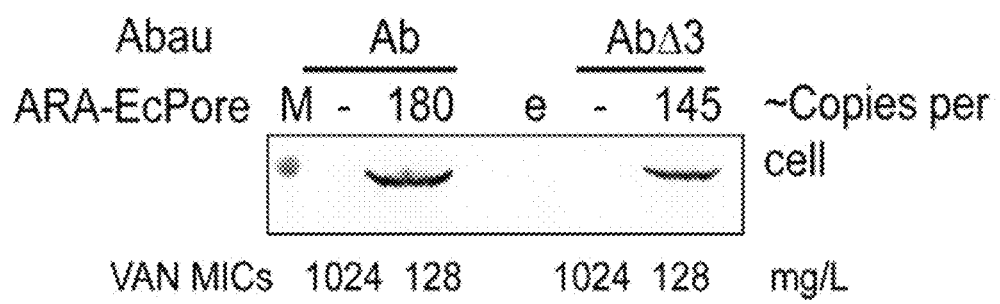

Contributions of the diffusion barrier and active efflux in antibacterial activities can be separated by inserting a large non-specific pore into the OM to allow unrestricted influx of antibiotics (Krishnamoorthy et al., 2016, op cit.). To construct certain hyperporinated strains, the gene encoding the recombinant EcPore (FhuA ΔC/Δ4L) was integrated onto the chromosomes of P. aeruginosa PAO1 (Pae), A. baumannii ATCC17978 (Abau), B. thailandensis E264 (Bt) and B. cepacia ATCC25416 (Bc) (Table 2). As negative controls, empty expression cassettes were integrated into respective strains as well. Herein and hereinbelow, the names of the strains comprise the strain abbreviation followed by the inducible promoter used for the induction (ARA for arabinose, LAC for IPTG and RHA for rhamnose) and the name of the pore, if present. Genetic tests, the hypersusceptibility to the OM-impermeable antibiotic vancomycin and immunoblotting analyses confirmed the successful integration onto chromosomes and the inducer-dependent expression of the protein in PAO1-LAC-EcPore and Ab-ARA-EcPore (FIGS. 1A-1B). However, the protein failed to be expressed and function in Bt and Bc strains.

Figure 2A:
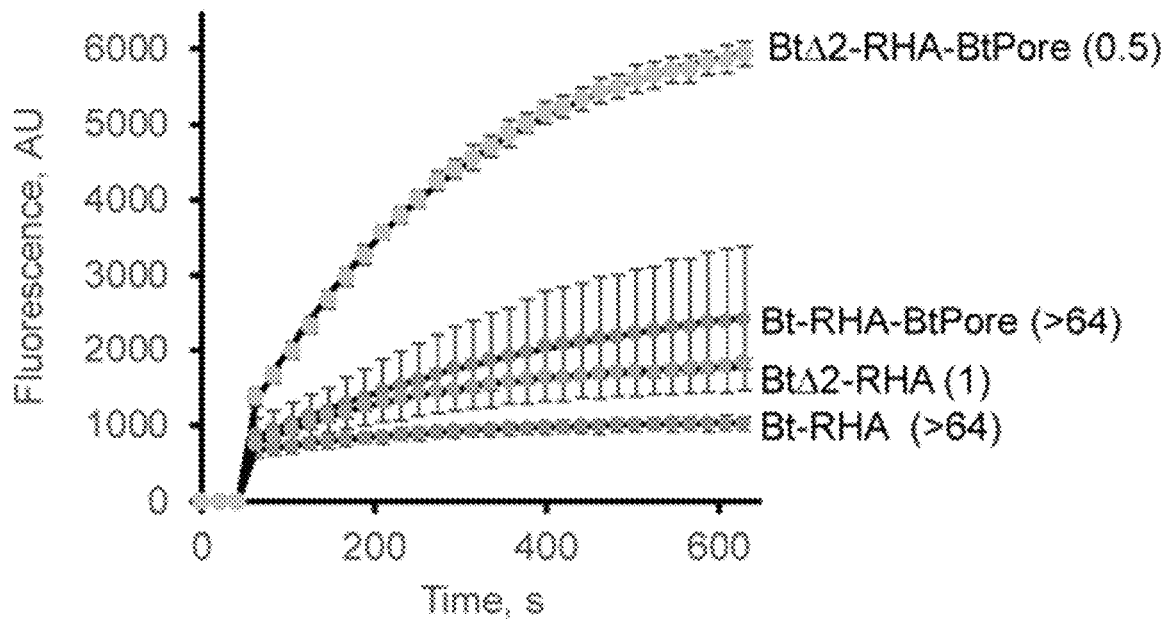
FIG. 2A shows intracellular accumulation and uptake of the DNA-binding fluorescent probe Hoechst 33342 (HT) in *B. thailandensis* and hyperporinated and/or efflux-deficient mutant derivatives thereof, including real-time kinetics of HT uptake. Bt-RHA represents the parent strain. Bt-RHA-BtPore represents the hyperporinated mutant. BtΔ2-RHA represents the efflux-deficient mutant. BtΔ2-RHA-BtPore represents the ef ratios in WT and efflux mutants with either native membranes (Bt, Abau, PAO1 and *E. coli*) or hyperporinated outer membranes (Bt-Pore, Abau-Pore, PAO1-Pore and *E. coli*-Pore) are shown. The scale of $\log_2$(fold change in MICs) is shown.
Figure 2B:
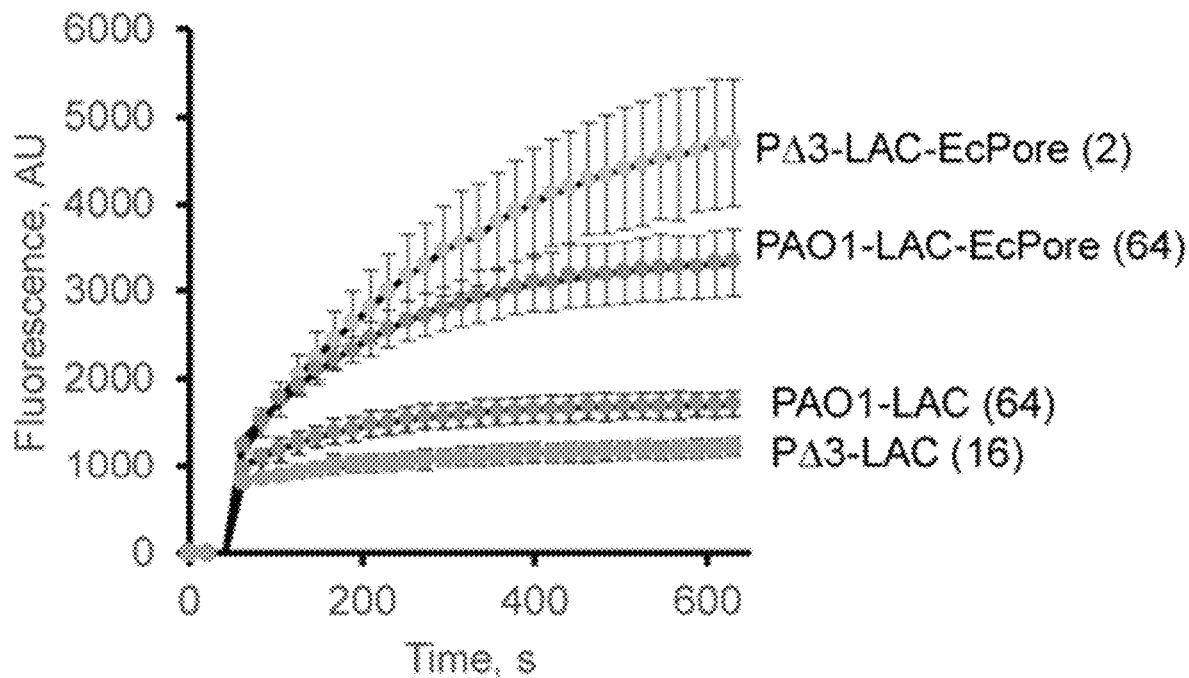
Figure 2C:
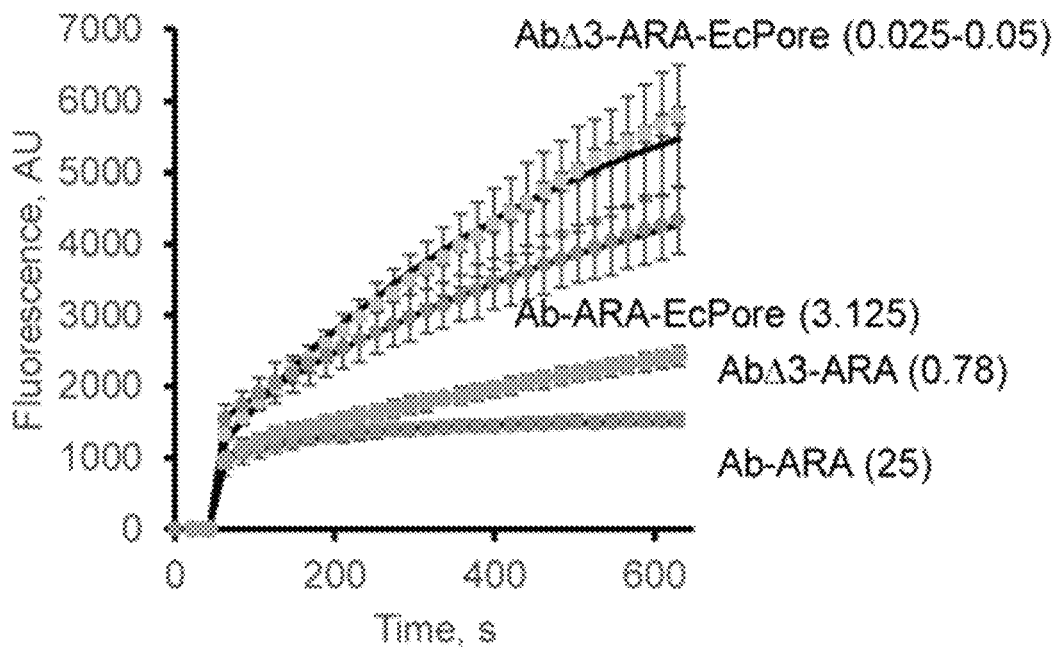
Figure 2D:
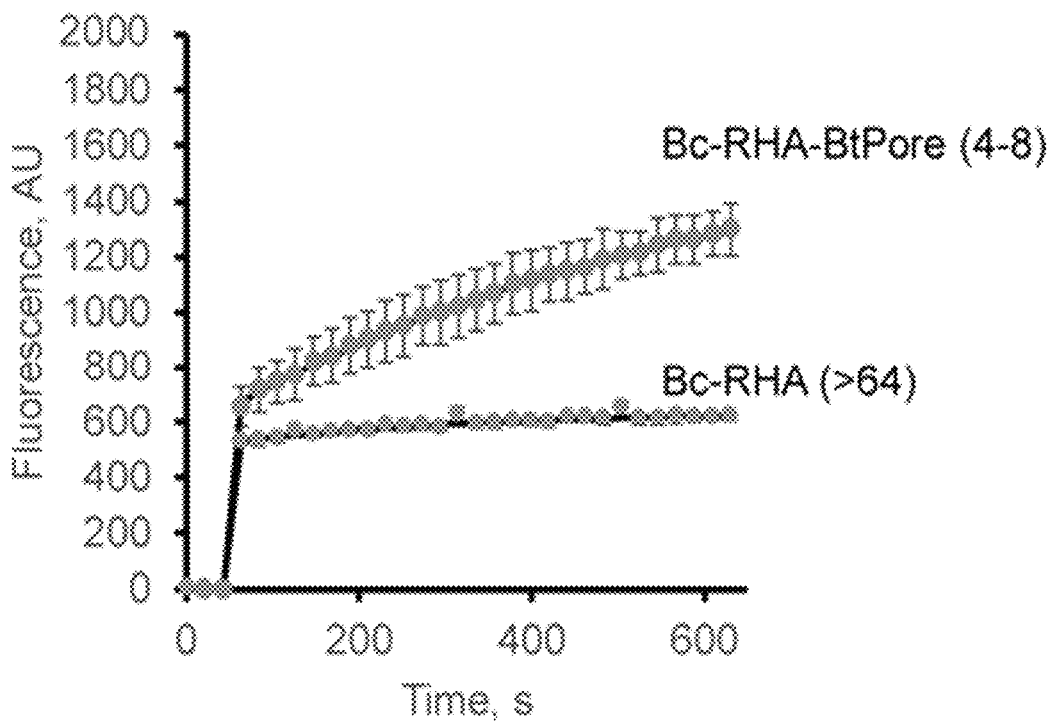

We next designed a pore (BtPore) using the OrbA siderophore uptake channel (Sokol P A, Darling P, Lewenza S, Corbett C R, Kooi C D. 2000, Identification of a Siderophore Receptor Required for Ferric Ornibactin Uptake in Burkholderia cepacia Infection and Immunity 68:6554-6560.) from Bt as a template. To improve the expression, a synthetic gene encoding BtPore protein was cloned downstream of the rhamnose-inducible promoter (RHA). Genetic tests showed that the gene encoding BtPore was integrated into gimS sites present on the Bt (Bt-RHA-BtPore) and Bc (Bc-RHA-BtPore) chromosomes. The protein was expressed in a rhamnose-dependent manner, was localized to the OM fractions and enabled vancomycin-dependent killing of cells (FIG. 1C).

The genes encoding EcPore and BtPore were further integrated onto the chromosomes of efflux-deficient variants of Pae, Abau and Bt, correspondingly. PaΔ3-LAC and PaΔ3-LAC-EcPore cells are deficient in mexAB, mexCD and mexXY, the inner membrane components of the major RND pumps of this species. BtΔ2-RHA and BtΔ2-RHA-BtPore strains lack the two RND type pumps AmrAB-OpmA and BpeAB-OpmB that were previously reported to be constitutively expressed and to contribute to the intrinsic antibiotic resistance in *Burkholderia* spp. To analyze the role of efflux in Abau, we constructed an isogenic strain AbΔ3 lacking AdeIJK, AdeAB and AdeFGH, the three characterized RND efflux pumps of this species. For all constructed strains (Table 2), incubation of cells in the presence of respective inducers did not affect growth rates or cell densities suggesting that hyperporination of all four species and their efflux-deficient strains does not result in significant growth defects (FIGS. 6A-6C). In agreement, the morphology of hyperporinated cells and the protein contents of the inner and outer membranes were indistinguishable from the cells without pores (FIGS. 6A-6C). Quantitative immunoblotting analyses (FIGS. 1A-1C) showed that Pae, Bt and Bc produce comparable amounts, 2-10 copies per cells, of pore proteins in the OM. In contrast, the amounts of EcPore in Abau cells were significantly higher at 150-200 copies per cell and were comparable to those previously reported in *E. coli* (Krishnamoorthy et al., 2016, op cit.).

Intracellular Accumulation of Fluorescent Probes is defined by Differences in Permeability Barriers.

Active efflux is effective because drugs are expelled across the low permeability barrier of the OM. Hence, increased influx across the OM could significantly diminish or even obliterate the contribution of active efflux. On the other hand, inactivation of efflux is expected to completely eliminate the permeability barrier in non-growing cells, because the outer membrane slows down but does not prevent the diffusion. To analyze the interplay between passive influx and active efflux in permeation of compounds and to establish whether hyperporination affects diverse species in the same manner, we measured kinetics of intracellular accumulation of two fluorescent probes Hoechst 33342 (HT) and N-phenyl-1-naphthylamine (NPN). The two probes are known substrates of bacterial efflux pumps, but have different physicochemical properties and intracellular binding sites. HT is an inhibitor of DNA topoisomerases with MICs in a low micromolar range in efflux-deficient strains (Tables 7-9). The fluorescence of water-soluble HT is significantly enhanced when the compound is bound to lipids and DNA. NPN is a lipophilic, non-toxic compound, which is fluorescent when bound to biological membranes.

In these experiments, induced cells were suspended in buffered glucose solution, supplemented with either HT or NPN. In all four species, the overall kinetics of HT accumulation was similar (FIGS. 2A-2D). Following the initial burst, caused by binding to cell membranes, HT fluorescence steadily increased reflecting the cytoplasmic accumulation of DNA-bound HT (FIGS. 2A-2D). However, the species differed significantly in the rates and intracellular accumulation levels of HT. In Bt-RHA and Bc-RHA cells, the initial binding of HT to membranes was at least 2-3 times lower than in Pae and Abau cells, suggesting that cell envelopes of these species are significantly less permeable to HT (FIGS. 2A and 2D). In all species, hyperporination increased the influx across the OM by at least 2-4 times, as seen from the increased intracellular accumulation of HT in the strains producing the pores (FIGS. 2A-2D). The pore-mediated increase in HT accumulation was the largest in PAO1-LAC-EcPore and Ab-ARA-EcPore cells and resulted in a corresponding 4 to 8-fold drop of HT MICs in these cells (FIGS. 2B and 2C). The increase in the accumulation of HT was smaller and similar in Bt-RHA-BtPore and Bc-RHA-BtPore, but only hyperporination of Bc resulted in a measurable, >4-fold decrease in the MIC. Thus, the total intracellular HT concentration, as measured by changes in HT fluorescence, and the concentration of external HT needed to inhibit the target, as measured by MICs, relate to each other in a complex, indirect manner.

Inactivation of efflux led to a smaller, up to 2-fold increase of intracellular HT accumulation in Bt and Abau, whereas PΔ3-LAC cells accumulated HT at the levels lower than those in the parent PAO1-LAC. Thus, inactivation of efflux and hyperporination have different effects on the penetration of HT across the cell envelope. However, in all species, efflux-deficient hyperporinated cells accumulated the highest amounts of HT and were the most susceptible to the antibacterial activity of HT with MICs at 25-50 nM in AbΔ3-ARA-EcPore and 0.5 M and 2.0 μM in BtΔ2-RHA-BtPore and PΔ3-LAC-EcPore, respectively.

Thus, in all species, active efflux remains functional in hyperporinated cells and reduces intracellular accumulation of HT despite increased influx of the probe across the outer membrane. At the same time, inactivation of efflux reduces the permeability barrier only partially and the slow uptake across the outer membrane defines the rates of penetration. The changes in rates of uptake in hyperporinated cells without active efflux appear to be different from the uptake rates in cells either producing the pore or lacking efflux pumps, suggesting synergistic relationships. The exact changes in MICs of HT could be calculated only in the case of Abau (Table 9). Impressively, inactivation of efflux in Abau reduces the MIC of HT by 32 fold, hyperporination by 8 fold, whereas AbΔ3-ARA-EcPore are 1000-fold more susceptible to HT than Ab-ARA. Thus, the effect of the active efflux and the permeability barrier on the HT uptake and its antibacterial activity is synergistic.

Figure 3A:
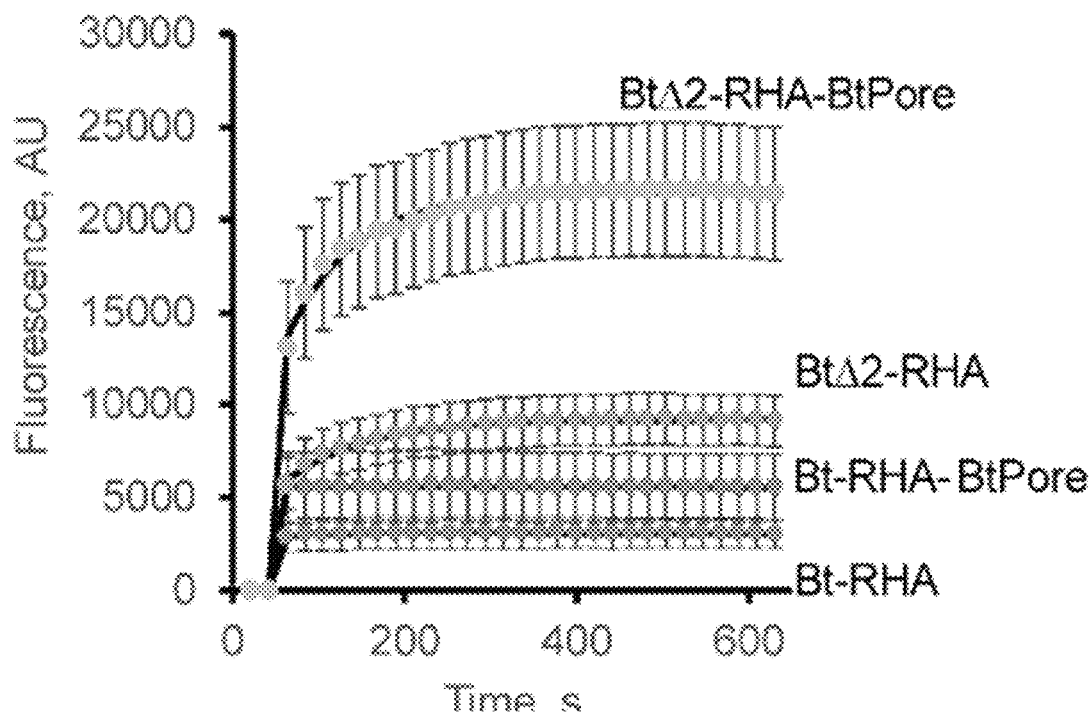
Figure 3B:
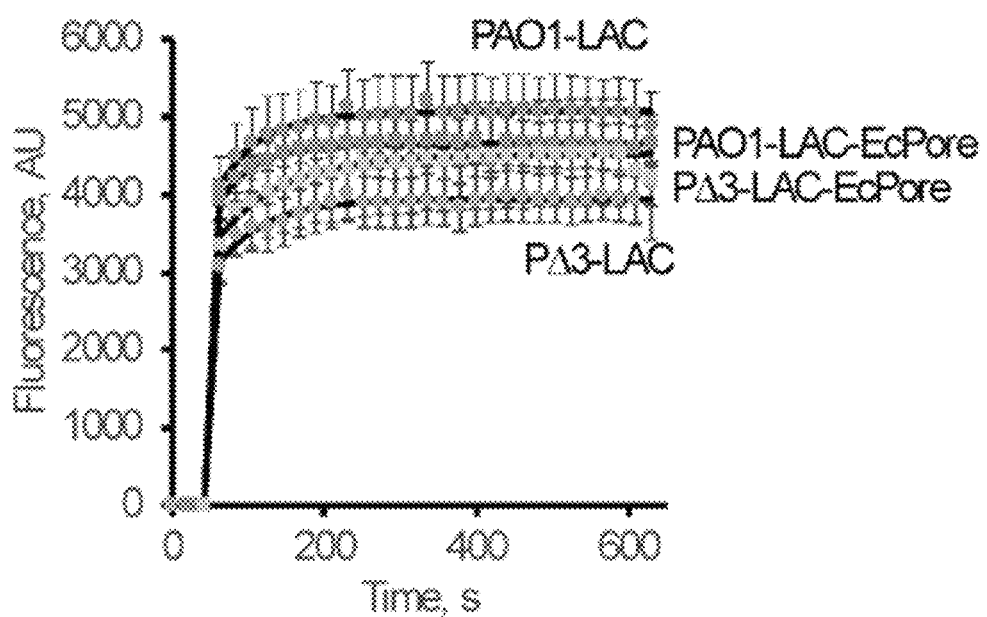
Figure 3C:
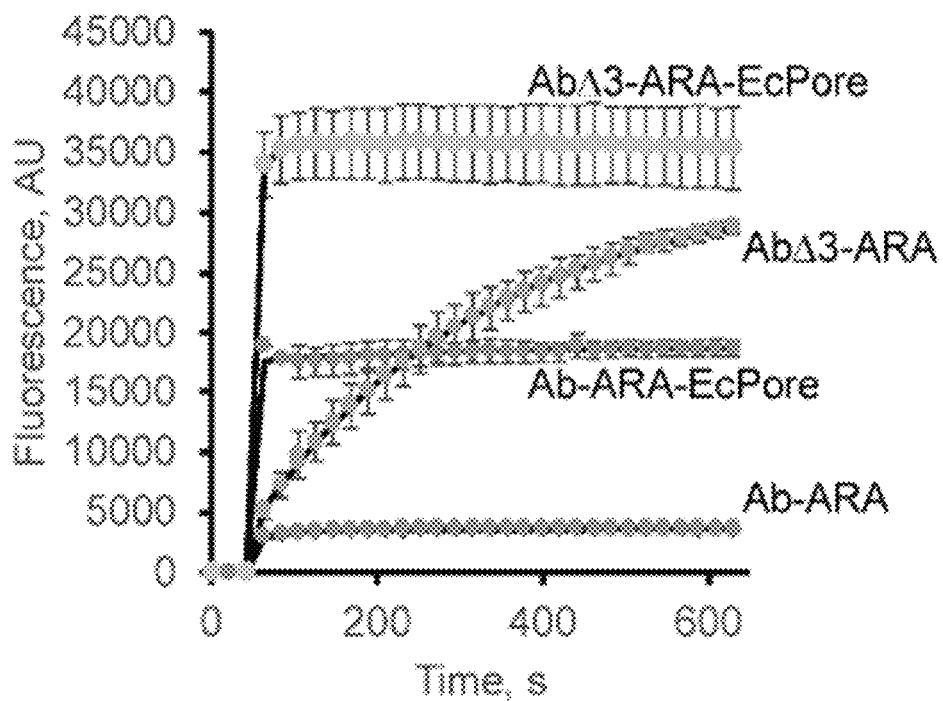
Figure 3D:
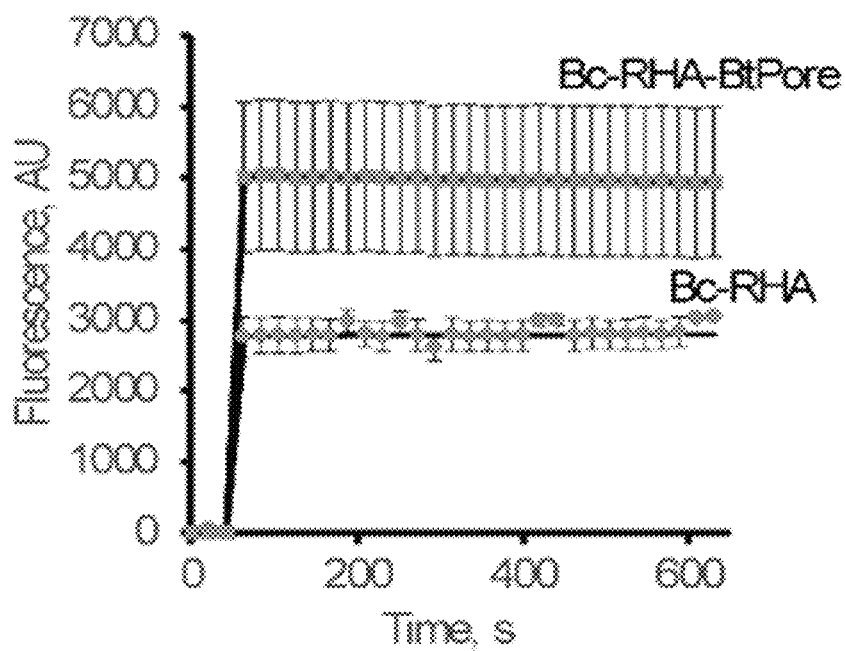

The results described above also show that the effect of hyperporination and efflux inactivation on HT accumulation is species-specific, as can also be seen in accumulation of NPN, a membrane-binding dye (FIGS. 3A-3D). Hyperporination increased the accumulation of NPN in Bt and Bc membranes only modestly by about two times (FIGS. 3A and 3D) but resulted in a large, more than six-fold increase in NPN levels in Abau membranes (FIG. 3C). On the other hand, no significant changes in NPN levels could be seen in hyperporinated PAO1-LAC-EcPore cells (FIG. 3B). Unlike with HT, the loss of active efflux in Bt and Abau resulted in higher levels of NPN accumulation than in hyperporinated cells (FIGS. 3A and 3C), suggesting that the outer membranes of these species are more permeable to this probe and efflux plays the dominant role. In particular, the outer membrane of efflux-deficient AbΔ3-ARA did not impose a significant permeability barrier for NPN as seen from continuous accumulation of this probe inside the cells over the time-course of the experiment. Surprisingly, the NPN levels in the efflux-deficient hyperporinated PΔ3-LAC-EcPore cells were only slightly higher than in PAO1-LAC cells. This result suggests that in Pae cells, this hydrophobic probe binds to the OM and does not reach the inner membrane during the time course of these experiments.

Taken together, these results show that the four Gram-negative species are protected by permeability barriers that differ significantly in their properties. Either hyperporination or efflux inactivation lead to species-specific changes in the kinetics of intracellular accumulation of fluorescent probes. The interplay between active efflux and the permeability barrier of the OM generate strong synergistic effects.

Synergism of Active Efflux and Passive Uptake in Antibacterial Activities.

The results described above show that hyperporination and efflux inactivation have different effects on compound accumulation and that these effects are also specific to bacterial species. We next analyzed interplay between active efflux and transmembrane diffusion in antibacterial activities of compounds with widely diverse physicochemical properties and mechanisms of action. We found that antibacterial activities of all tested antibiotics were affected in a species-specific manner by efflux inactivation, hyperporination or both (Tables 7-9).

TABLE 7

Susceptibilities to antibiotics of *P. aeruginosa* wild type and efflux-deficient strains and their hyperporinated variants.

| | MIC (μg/ml)[a] | | | |
|---|---|---|---|---|
| Antibiotic | PAO1-LAC | PAO1-LAC-EcPore | PaΔ3-LAC | PaΔ3-LAC-EcPore |
| Bacitracin | >1024 | 64 | >1024 | 64 |
| Zeocin | 512 | 32-64 | 16 | 2 |
| Rifampin | 16 | 0.5 | 16 | 0.5 |
| Vancomycin | 1024 | 128 | 1024 | 64 |
| Polymyxin B | 1.5 | 1.5 | 1.5 | 1.5 |
| Nalidixic acid | 64 | 32 | 8 | 2 |
| Levofloxacin | 0.125 | 0.063 | 0.031 | 0.004 |
| Ciprofloxacin | 0.063 | 0.031 | 0.016 | 0.004 |
| Amikacin | 2 | 2 | 1 | 1 |
| Tobramycin + $Mg^{2+}$ | 2 | 1 | 0.5 | 0.5 |
| Azithromycin | 128 | 4 | 4 | 0.063 |
| Erythromycin | 128 | 2 | 16 | 0.125 |
| Tetracycline | 4 | 0.5 | 2 | 0.125 |
| Ampicillin | 256 | 16 | 64 | 4 |
| Carbenicillin | 32 | 2 | 1 | 0.125 |
| Cloxacillin | >2048 | 512 | 128 | 8 |
| Novobiocin | 512 | 64 | 32 | 4 |
| Chloramphenicol | 8 | 2 | 1 | 0.125 |
| Triclosan | 1024 | 1024 | 32 | 8 |
| HT | >64 | 64 | 16 | 2 |
| Meropenem | 0.5 | 0.25 | 0.125 | 0.03 |

[a]At least three independent measurements

TABLE 8

Minimal inhibitory concentrations of antibiotics in *B. thailandensis* wild type and efflux-deficient strains and *B. cepacia* and their hyperporinated variants.

| | MIC (mg/L)$^a$ | | | | | |
|---|---|---|---|---|---|---|
| Antibiotics | Bt-RHA | Bt-RHA-BtPore | BtΔ2-RHA | BtΔ2-RHA-BtPore | Bc-RHA | Bc-RHA-BtPore |
| Bacitracin | >1024 | 1024 | 1024 | 8 | >1024 | 16 |
| Zeocin | 512 | 128 | 2 | 0.12 | >1024 | 128 |
| Rifampin | 16 | 8 | 4 | 0.03 | 8 | 0.06 |
| Vancomycin | >1024 | 256-512 | >1024 | 4-8 | >1024 | 8 |
| Polymyxin B | >1024 | >1024 | >1024 | 128 | >1024 | 512 |
| Nalidixic acid | 48 | 24 | 12 | 1.5 | 24 | 3 |
| Levofloxacin | 2 | 1 | 0.06 | 0.0156 | 2 | 0.06 |
| Ciprofloxacin | 1 | 0.5 | 0.06 | 0.016 | 1 | 0.03 |
| Gentamicin | >64 | >64 | 4 | 2 | 128 | 16 |
| Amikacin | 256 | 256 | 4 | 2 | 128 | 8 |
| Kanamycin | >64 | 64 | 4 | 2 | 64 | 4-8 |
| Tobramycin+ Mg$^{2+}$ | 64 | 64 | 1 | 1 | 32-64 | 4 |
| Azithromycin | 128 | 64 | 1 | 0.032 | 64 | 1-2 |
| Erythromycin | 512 | 256 | 1 | 0.5 | 256 | 8-16 |
| Tetracycline | 2 | 2 | 0.125 | 0.06 | >8 | 8 |
| Doxycycline | 3 | 1.5 | 0.02 | 0.01 | 6 | 3 |
| Ampicillin | 256 | 256 | 256 | 4 | >1024 | 512 |
| Carbenicillin | 256-512 | 256 | 256 | 8 | >1024 | 128 |
| Cloxacillin | 256 | 128-256 | 32 | 0.5 | 256 | 4 |
| Novobiocin | 8 | 4 | 0.25 | 0.008 | 8 | 0.125 |
| Chloramphenicol | 8 | 8 | 4 | 1 | 16 | 4 |
| Triclosan | 120 | 30 | 0.12 | 0.06 | >120 | 60 |
| HT (μm) | >64 | >64 | 1 | 0.5 | >64 | 4-8 |
| Meropenem | 1 | 1 | 0.25 | 0.03 | >4 | 0.125 |

TABLE 9

Minimal inhibitory concentrations of antibiotics in *A. baumannii* wild type and efflux-deficient strains and their hyperporinated variants.

| | MIC (mg/L)$^a$ | | | |
|---|---|---|---|---|
| Antibiotics | Ab-ARA | Ab-ARA-EcPore | AbΔ3-ARA | AbΔ3-ARA-EcPore |
| Bacitracin | 256 | 32 | 512 | 64 |
| Zeocin | 8 | 0.5 | 1 | 0.125 |
| Rifampin | 2 | 0.5 | 1 | 0.25 |
| Vancomycin | 1024 | 128 | 1024 | 128 |
| Polymyxin B | 0.25 | 0.25 | 0.125 | 0.125 |
| Nalidixic acid | 3 | 1.5 | 1.5 | 0.75 |
| Levofloxacin | 0.125 | 0.125 | 0.031 | 0.031 |
| Ciprofloxacin | 0.063 | 0.008 | 0.008 | 0.004 |
| Gentamicin | 4 | 4 | 8 | 8 |
| Amikacin | 8 | 4 | 4 | 4 |
| Tobramycin + Mg$^{2+}$ | 4 | 2 | 4 | 2 |
| Azithromycin | 0.31 | 0.04 | 0.31 | 0.08 |
| Erythromycin | 5 | 1.25 | 1.25 | 0.08 |
| Tetracycline | 0.125 | 0.031 | 0.008 | 0.004 |
| Doxycycline | 0.04 | 0.02 | 0.0016 | 0.0016 |
| Ampicillin | 2048 | 128 | 1024 | 128 |
| Carbenicillin | 2048 | 32 | 2048 | 64 |
| Cloxacillin | 1024 | 128 | 128 | 16 |
| Novobiocin | 3.1 | 1.56 | 0.025 | 0.025 |
| Chloramphenicol | 32 | 8 | 8 | 4 |
| Triclosan | 0.125 | 0.063 | 0.002 | 0.001 |
| HT | 25 | 3.125 | 0.78 | 0.025 |
| Meropenem | 0.25 | 0.063 | 0.125 | 0.063 |

$^a$At least three independent measurements

TABLE 10

Coordinates and the explained variance of the principal components analysis (PCA).

| | 1 | 2 | 3 | 4 | 5 | 6 | 7 | 8 | 9 | 10 | 11 | 12 | 13 |
|---|---|---|---|---|---|---|---|---|---|---|---|---|---|
| PCA Component | | | | | | | | | | | | | |
| Explained Variance | 0.390 | 0.250 | 0.125 | 0.074 | 0.056 | 0.038 | 0.034 | 0.015 | 0.010 | 0.004 | 0.002 | 0.001 | 0.000 |
| Cumulative Explained Variance | 0.390 | 0.640 | 0.766 | 0.840 | 0.896 | 0.934 | 0.968 | 0.983 | 0.992 | 0.997 | 0.999 | 1.000 | 1.000 |
| PCA variable | | | | | | | | | | | | | |
| PAO1/PAO1-Pore | 0.296 | 0.211 | −0.042 | −0.260 | 0.452 | 0.120 | −0.040 | 0.128 | 0.037 | 0.610 | 0.073 | 0.317 | −0.287 |

TABLE 10-continued

Coordinates and the explained variance of the principal components analysis (PCA).

| | 1 | 2 | 3 | 4 | 5 | 6 | 7 | 8 | 9 | 10 | 11 | 12 | 13 |
|---|---|---|---|---|---|---|---|---|---|---|---|---|---|
| PΔ3/PΔ3-Pore | 0.258 | 0.318 | −0.061 | −0.022 | 0.613 | −0.185 | 0.044 | 0.200 | −0.011 | −0.587 | −0.005 | −0.083 | 0.157 |
| PAO1/Δ3 | −0.031 | 0.383 | −0.140 | −0.345 | −0.470 | 0.046 | −0.039 | 0.588 | −0.151 | −0.041 | 0.120 | 0.186 | 0.263 |
| BT/BT-Pore | 0.045 | 0.103 | 0.054 | 0.010 | −0.101 | 0.114 | 0.216 | −0.147 | 0.068 | −0.193 | 0.868 | −0.025 | −0.310 |
| BTΔ2/BTΔ2-Pore | 0.454 | −0.017 | −0.245 | 0.057 | −0.149 | 0.314 | 0.613 | −0.251 | −0.259 | −0.064 | −0.198 | 0.200 | 0.142 |
| BT/BTΔ2 | −0.204 | 0.470 | 0.747 | −0.041 | 0.003 | 0.264 | 0.115 | −0.200 | −0.067 | −0.057 | −0.186 | 0.111 | 0.018 |
| AB/AB-Pore | 0.179 | 0.124 | −0.073 | −0.441 | −0.252 | −0.050 | 0.088 | −0.072 | 0.495 | −0.197 | −0.330 | −0.236 | −0.475 |
| ABΔ3/ABΔ3-Pore | 0.220 | 0.112 | −0.015 | −0.367 | 0.000 | 0.037 | −0.209 | −0.436 | 0.140 | 0.200 | 0.187 | −0.357 | 0.589 |
| AB/ABΔ3 | −0.143 | 0.376 | −0.102 | 0.356 | −0.053 | −0.466 | 0.431 | −0.005 | 0.415 | 0.299 | 0.011 | 0.010 | 0.182 |
| WT/WT-Pore | 0.443 | 0.004 | 0.154 | 0.216 | −0.241 | −0.231 | −0.416 | −0.181 | 0.227 | −0.171 | 0.020 | 0.576 | 0.052 |
| ΔTolC/ΔTolC-Pore | 0.480 | −0.025 | 0.383 | 0.101 | −0.178 | −0.395 | 0.055 | 0.193 | −0.389 | 0.190 | 0.013 | −0.419 | −0.145 |
| WT/ΔTolC | −0.040 | 0.553 | −0.403 | 0.304 | −0.101 | 0.076 | −0.364 | −0.278 | −0.321 | 0.024 | −0.090 | −0.180 | −0.263 |
| BC/BC-Pore | 0.257 | 0.019 | 0.071 | 0.450 | −0.030 | 0.576 | −0.116 | 0.362 | 0.396 | 0.058 | −0.009 | −0.285 | 0.089 |

Figure 4A:
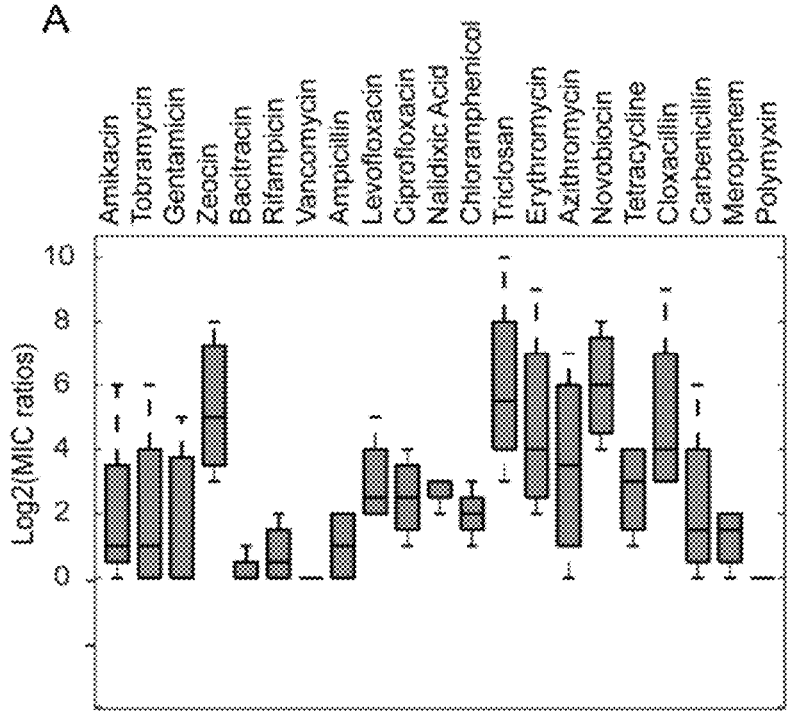
Figure 4B:
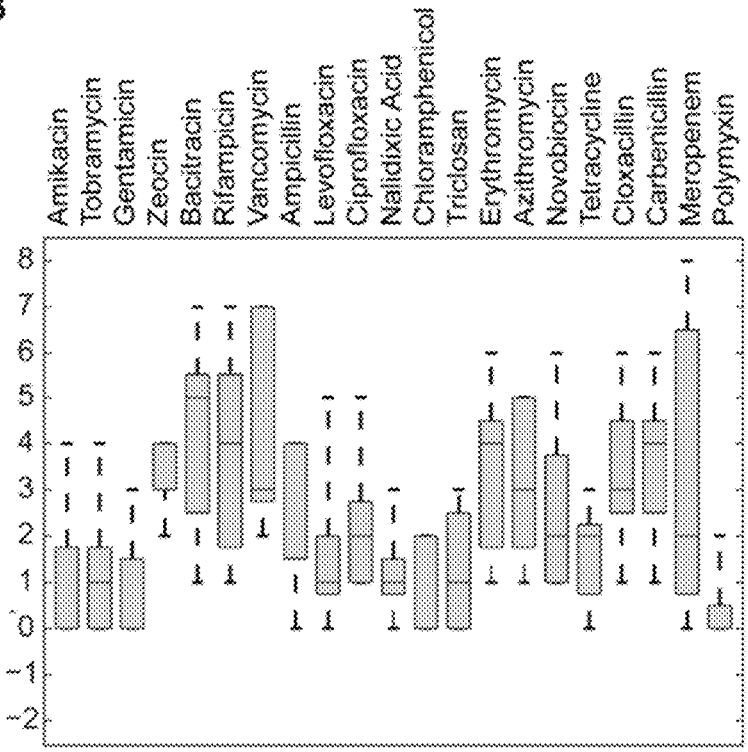

MIC ratios of parental and either efflux-deficient or hyperporinated cells, were calculated as appropriate. When grouped according to the effects of efflux inactivation (efflux ratios) and hyperporination (OM ratios), the MIC ratios displayed broad, species- and antibiotic-dependent variations (FIGS. 4A-4B). Notably, there was no obvious correlation between the consequences of transporter inactivation and hyperporination, indicating that the two effects are largely independent of each other. For example, in all species, fluoroquinolones, chloramphenicol, polymyxin and antibiotics with MW >800 Da were affected by efflux only weakly, as seen from narrow distributions of respective efflux ratios. In contrast, the OM ratios varied broadly for most antibiotics, with zeocin and polymyxin showing the narrowest distributions.

Figure 5A:
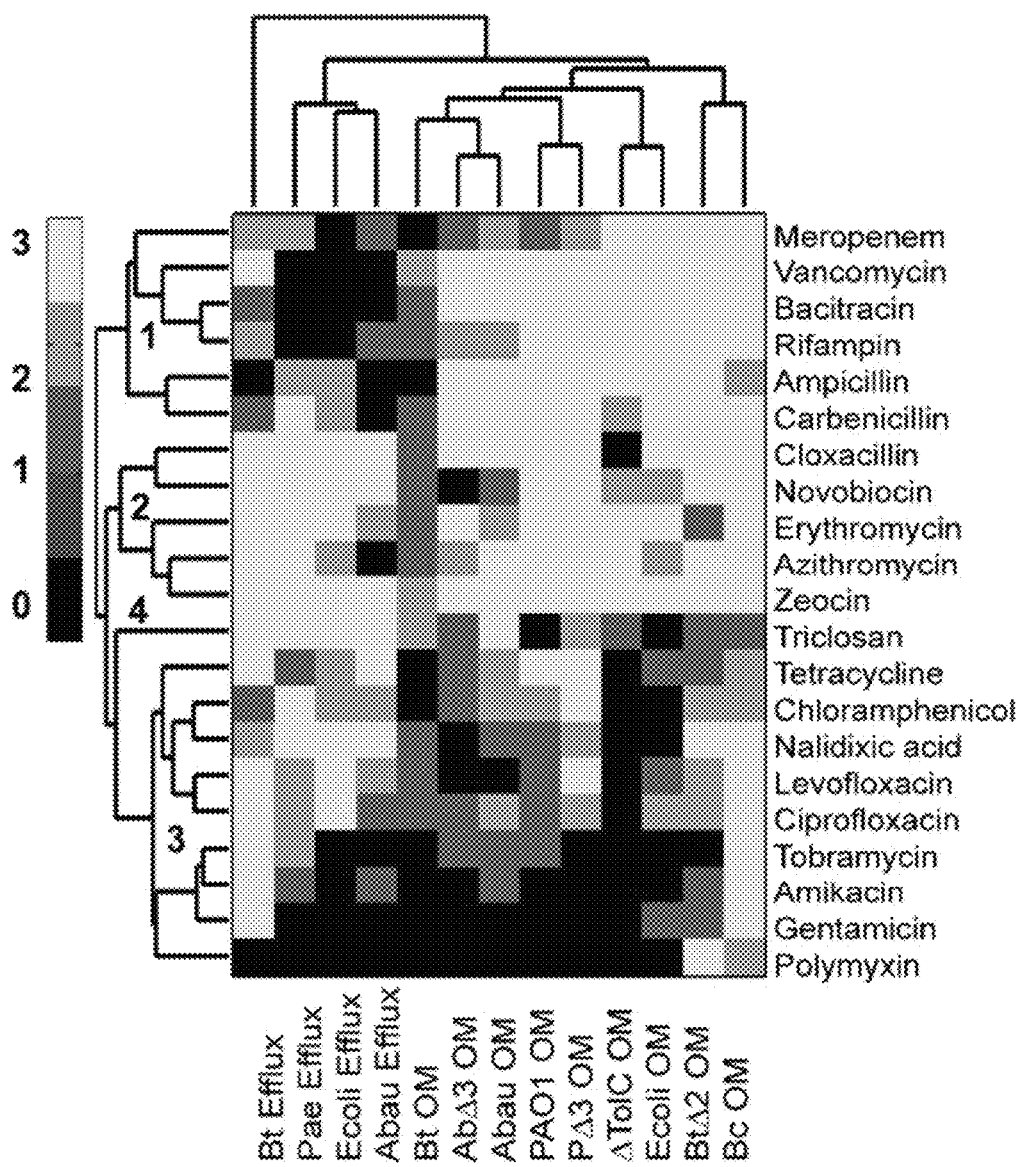
Figure 5B:
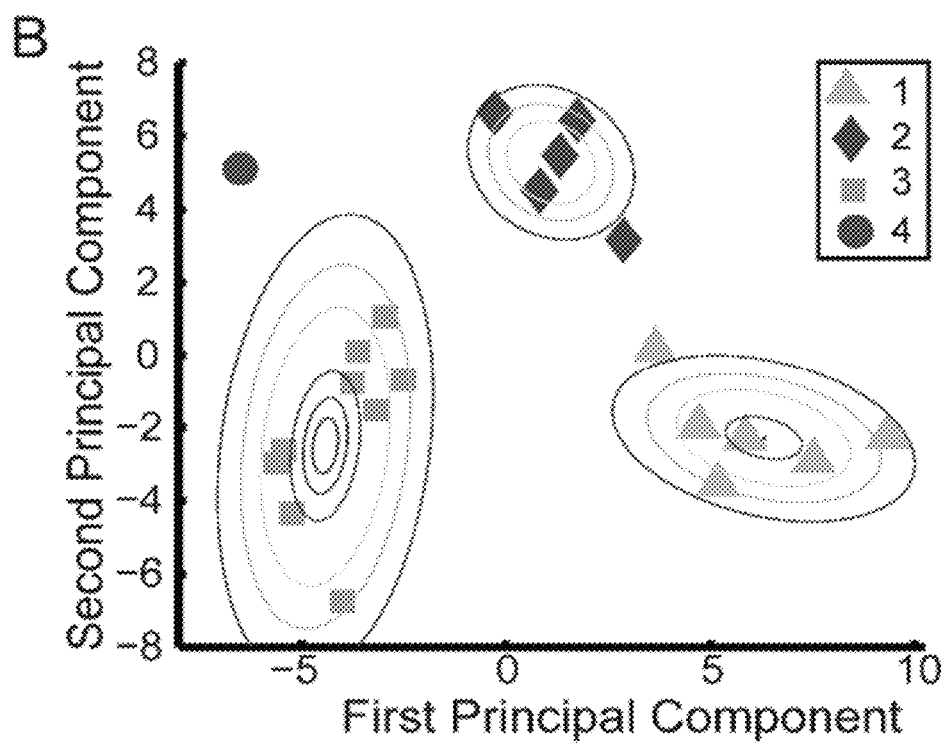

To reveal potentially hidden features in the accumulated data, we performed cluster analysis of the measured ratios. These analyses also included the MIC ratios determined previously in efflux-deficient and hyperporinated E. coli strains (Krishnamoorthy et al., 2016, op cit.). Strikingly, the tested antibiotics separated into several groups, which could be seen both in linkage analysis (FIG. 5A) and in principle component decomposition (FIG. 5B). Since clusterization is based on biological recognition, each group includes structurally diverse antibiotics belonging to different classes. The distinction between the groups was mainly based on the magnitude of the effects caused by efflux inactivation (PCA2) and hyperporination (PCA1) (FIG. 5B). Notably, the two effects were well separated from each other on the dendrogram (FIG. 5A), further pointing to their lack of interdependence. On the lower level, the effects of hyperporination on efflux-deficient and -proficient cells have clustered according to species. Hence, the distinction between effects of the pore on MICs appears to be driven by biological determinants.

The four clusters of antibiotics revealed by distance analysis were as follows. Group 1 comprises antibiotics that are strongly potentiated by hyperporination but not efflux inactivation in all species with the exception Bt that will be discussed below. This group includes vancomycin, bacitracin and rifampicin, as well as some beta-lactams (FIG. 5A). Vancomycin and bacitracin are large antibiotics with MW>1400 Da that target peptidoglycan synthesis but cannot permeate the OM. Rifampicin is a transcriptional inhibitor, which is large (850 Da) and hydrophobic. Beta-lactams are relatively hydrophilic and permeate the OM through porins. Thus, to cross the OM all these antibiotics must use porins or channels, which could be general or specific for different drugs and their activities are expected to be defined by biological determinants. Indeed, the OM ratios of the Group 1 antibiotics vary significantly between the species. For example, hyperporination significantly potentiated the activity of meropenem in Bc (>32 fold) but had a modest, 2-4 fold potentiation in other species. This result suggests that Bc lacks a specific OprD-like porin that facilitates the uptake of carbapenems in Pae and Abau.

Group 2 includes antibiotics, the antibacterial activities of which are strongly affected by both efflux inactivation and hyperporination. The Group 2 antibiotics are macrolides erythromycin and azithromycin, novobiocin, cloxacillin and zeocin (FIG. 5A). The MICs of these antibiotics vary broadly between the species reflecting species-specific differences in efflux capacities and OM selectivity (Tables 7-9). For example, Pae is resistant to novobiocin with MIC=512 mg/L, which contrasts with a relative susceptibility of Abau (MIC 3.1 mg/L), Bc (MIC 8 mg/L) and Bt (MIC 8 mg/L). Hyperporination resulted in only a modest 2-fold potentiation of novobiocin activity in Abau and Bt cells, but significant potentiation by 16-32-fold was found in Pae and Bc cells. The efflux ratios of novobiocin is high in all three Abau, Pae and Bt species. Surprisingly, in all species the antibacterial activity of zeocin, a glycopeptide antibiotic with the mass of 1428 Da was strongly affected by active efflux (Tables 7-9). The synergistic effect of inactivation of efflux pumps and hyperporination resulted in the staggering 64, 256 and 4096 fold change of the MIC of zeocin in AbΔ3-ARA-Pore, PaeΔ3-LAC-Pore and BtΔ2-RHA-Pore, respectively (Table 7-9).

Group 3 antibiotics were modestly affected by efflux or porination. This group comprises fluoroquinolones, tetracycline and chloramphenicol as well as polycationic aminoglycosides and polymyxin. These antibiotics either have small efflux and OM ratios, because they are able to penetrate permeability barriers of all species by avoiding efflux and diffusing across the OMs, or because they target the OM itself by binding and disintegrating the OMs in susceptible species. We found accordingly that neither inactivation of efflux nor hyperporination of OM, separately and combined, only weakly affected the bacterial susceptibilities to these antibiotics (Tables 7-9).

Finally, Group 4 was represented by only one antibiotic, triclosan, which uniquely showed a strong effect of efflux inactivation in all tested bacteria and a moderate effect of hyperporination. In general, a single point would not qualify to be called a cluster. However, triclosan (i) is well outside of the other three clusters, (ii) displays unique pattern of behavior, and (iii) is the furthest away from the rest of antibiotics on the clustering dendrogram. Analyses of a wider range of compounds will likely identify other members of this group. Thus, the found clusters produced clearly discernible patterns in respect to effects of efflux inactivation and hyperporination.

Clusterization based on, separately, the effects of the pore (FIGS. 8A and 8B) or efflux (FIGS. 8C and 8D) bore little resemblance to each other, in further support of the conclusion that the two factors act on antibacterial activities independently and are mechanistically unrelated. In both cases, however, the measurements for the same species were close together on the dendrograms (FIGS. 8A and 8C).

Figure 5C:
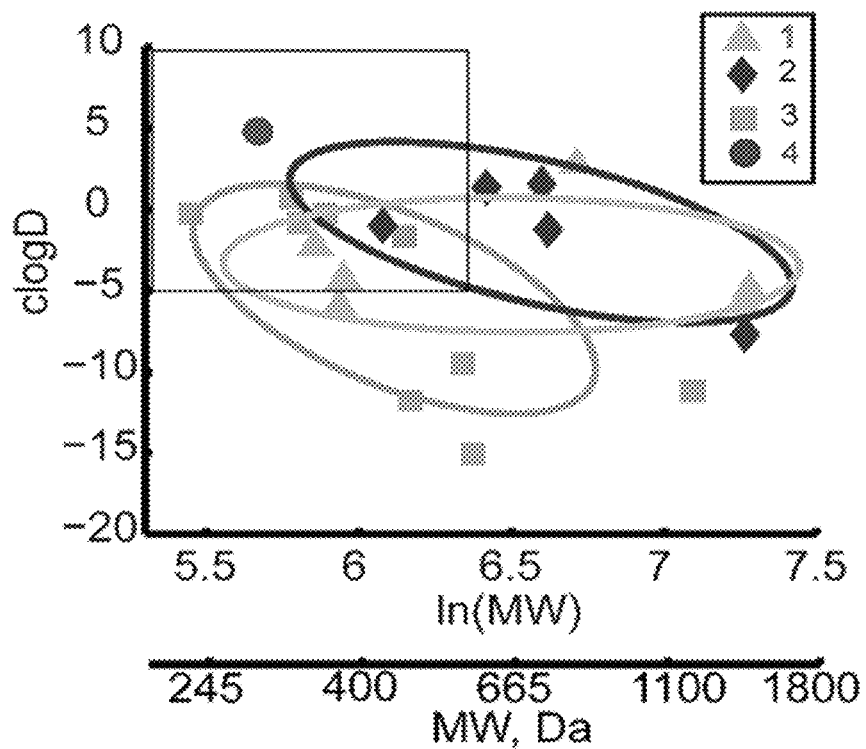
Figure 6A:
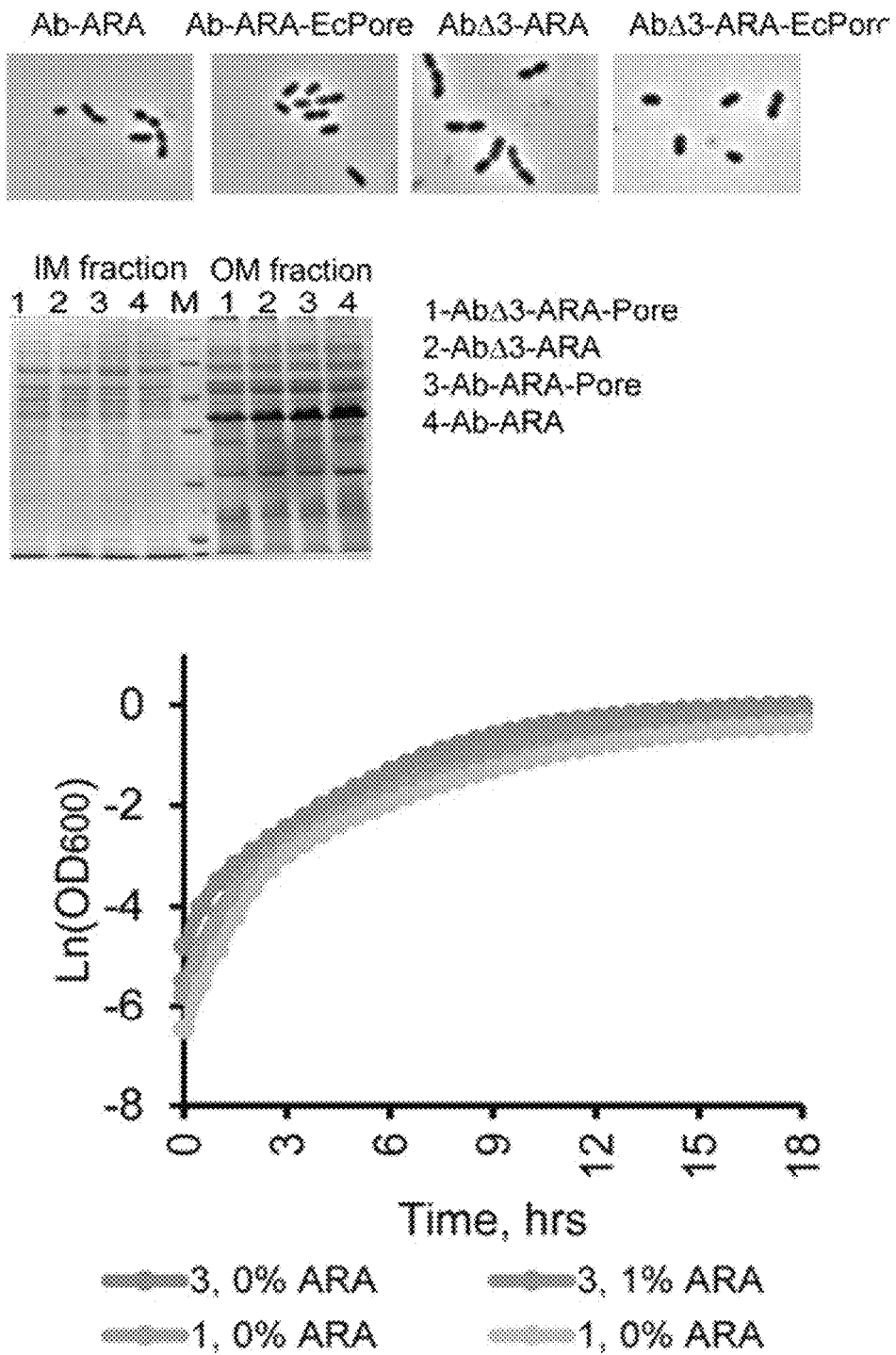
Figure 6B:
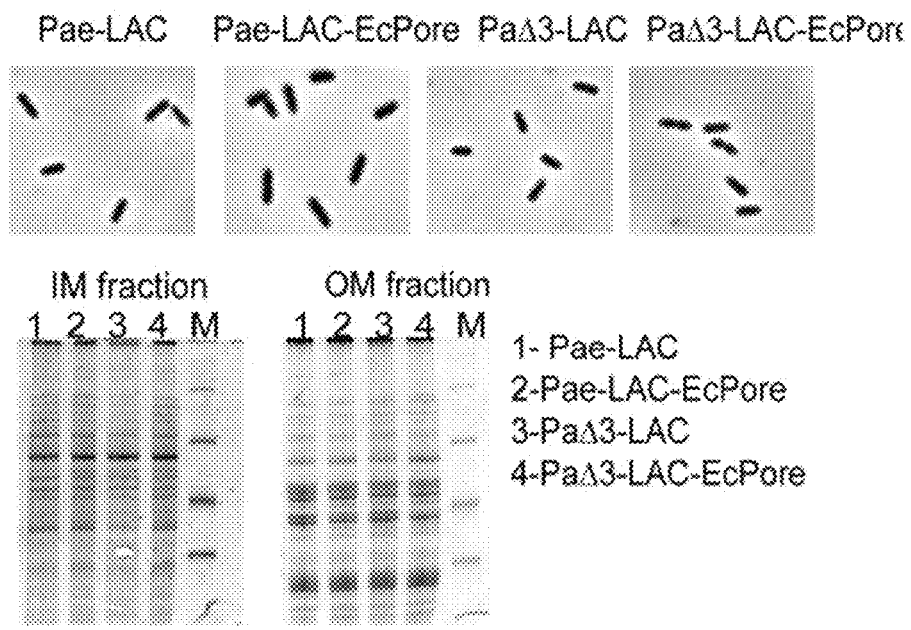
Figure 6B:
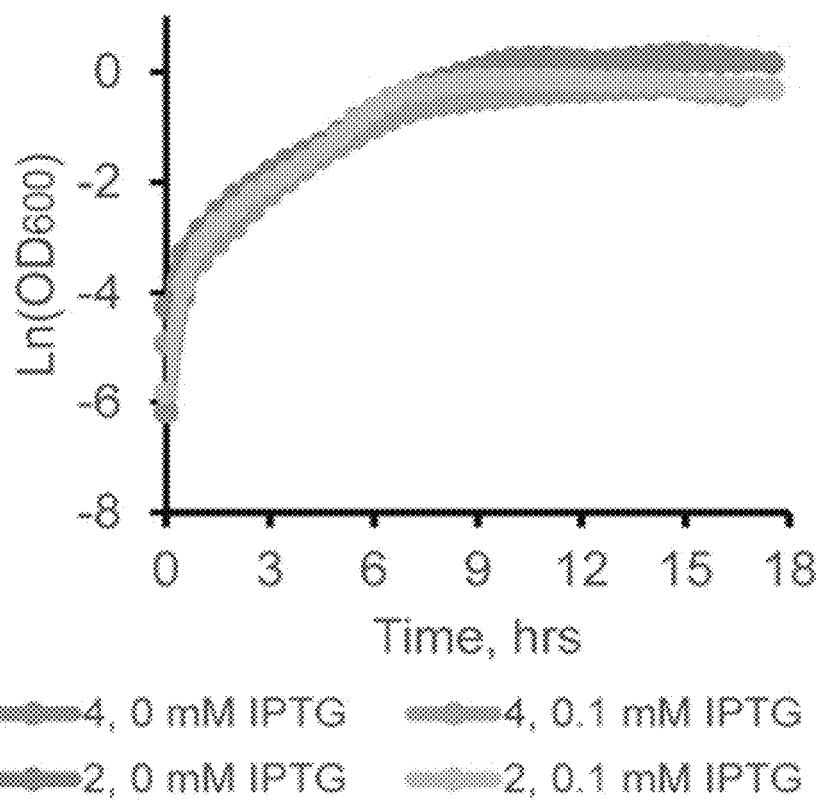
Figure 6C:
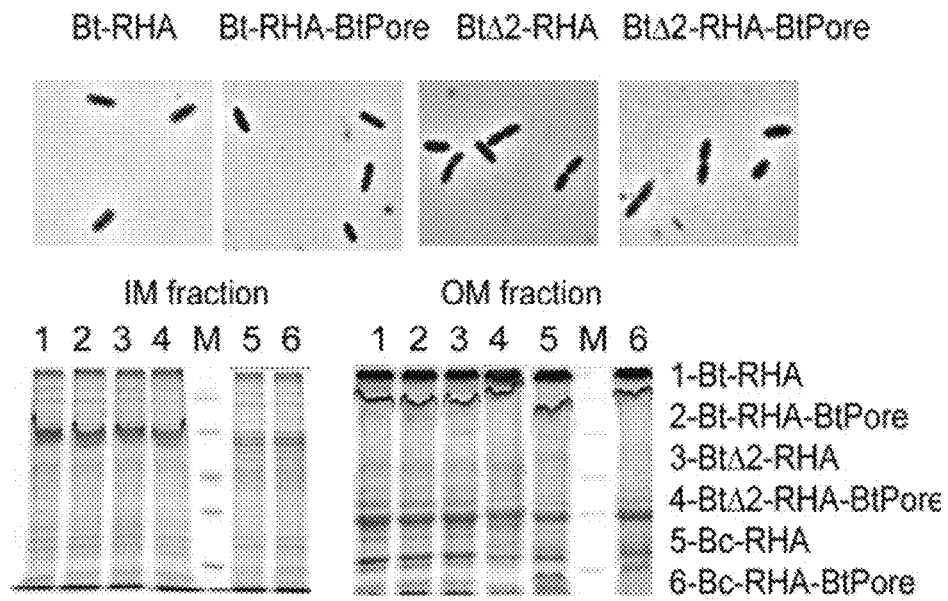
Figure 6C:
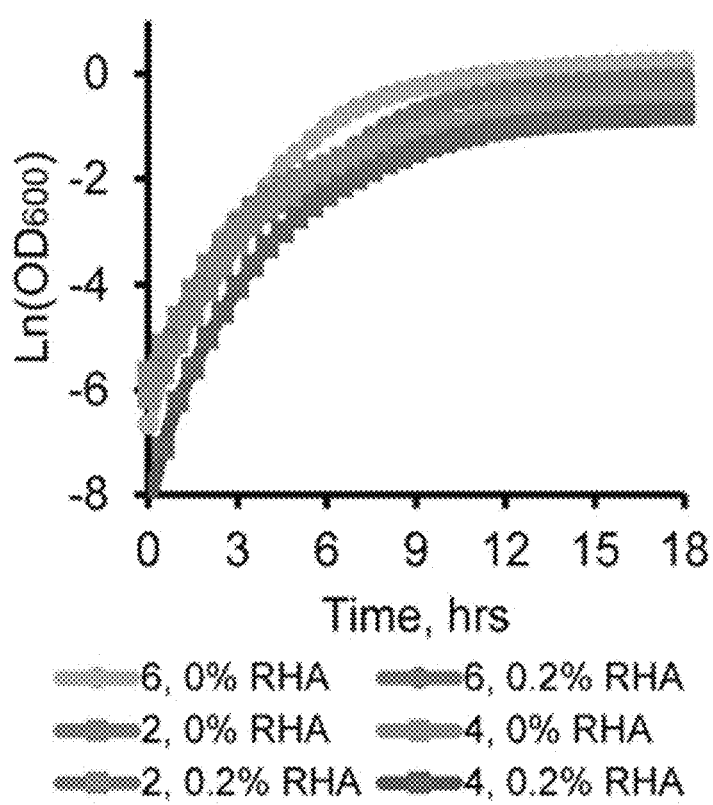
Figure 7A:
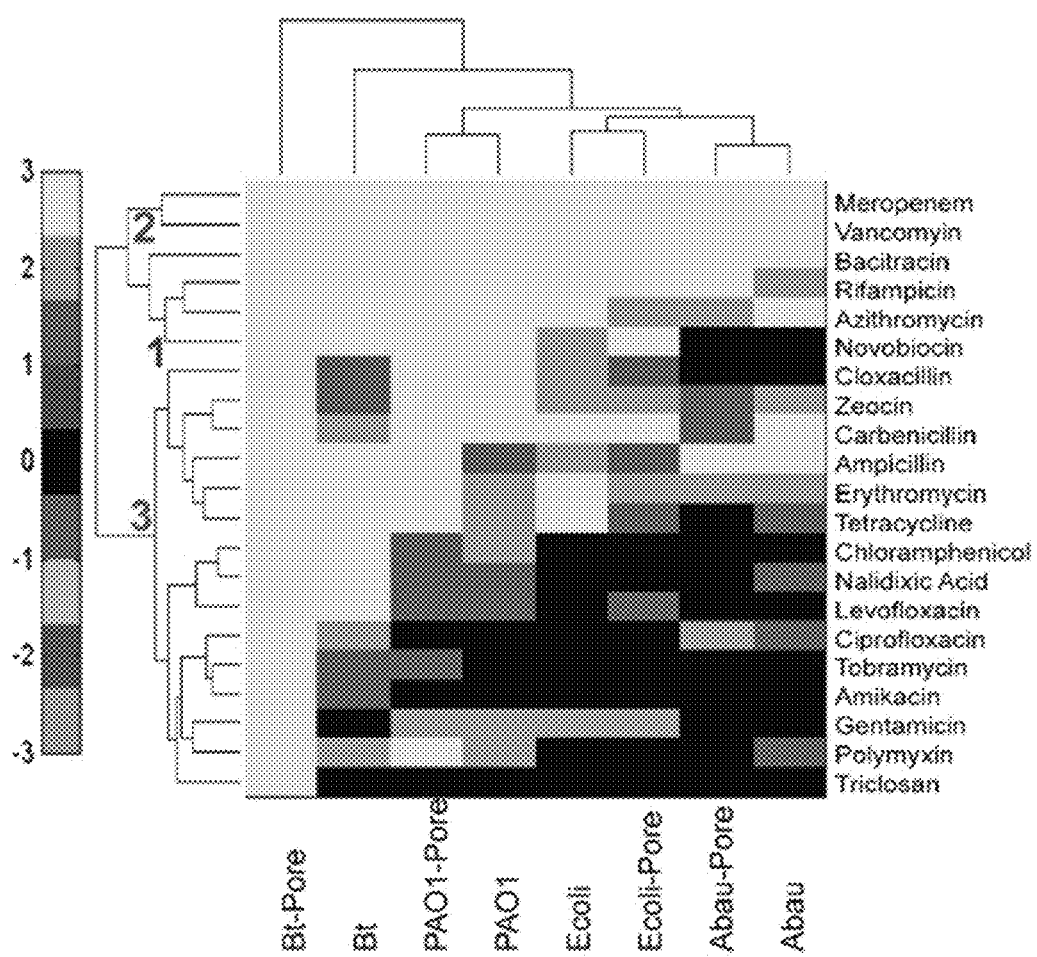
FIG. 7B shows a PCA of the efflux ratios of the strains and mutants of FIG. 7A. Clusters are numbered as for FIG. 7A.
FIG. 7C is a heat map of OM ratios in WT and pore mutants which are either efflux-proficient (Bt, Bc, Abau, PAO1 and *E. coli*) or efflux-deficient (AbΔ3, PΔ3, ΔTolC and BtΔ2). The scale of $\log_2$(fold change in MICs) is shown. The clusters of antibiotics are numbered.
FIG. 7D. PCA of the OM ratios of the strains and mutants of FIG. 7C. Clusters are numbered as for FIG. 7C.
Figure 7B:
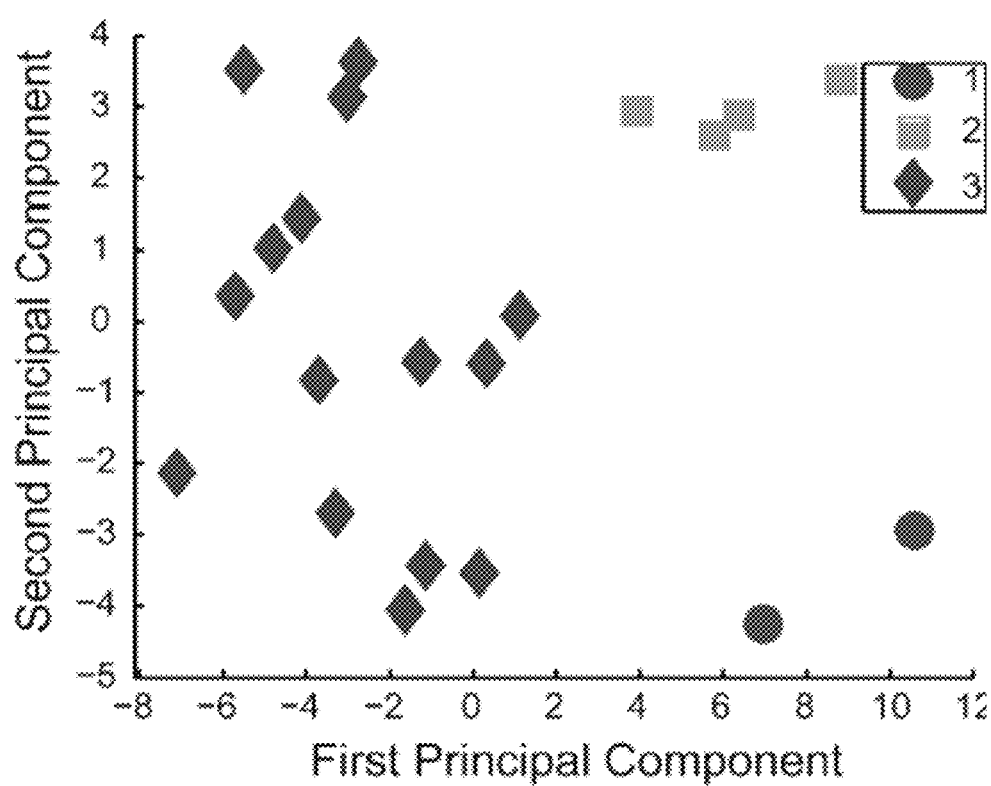
Figure 7C:
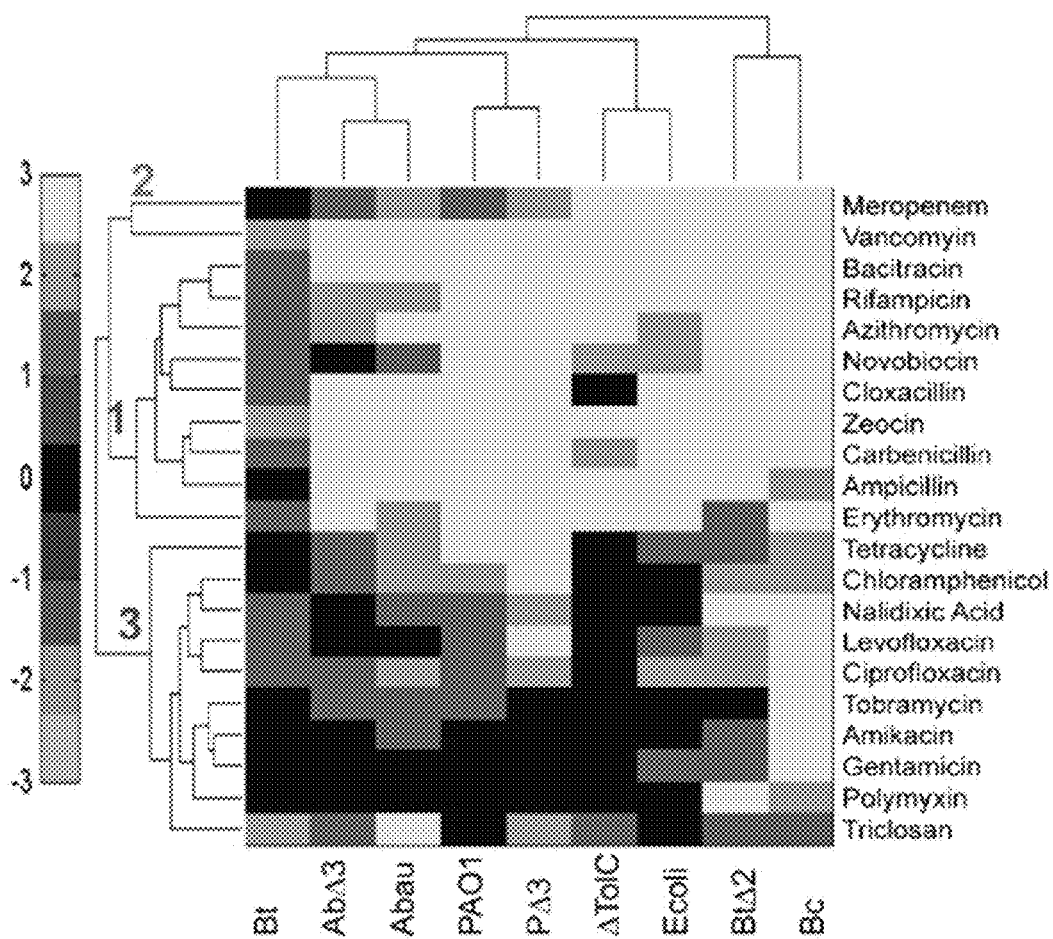
Figure 7D:
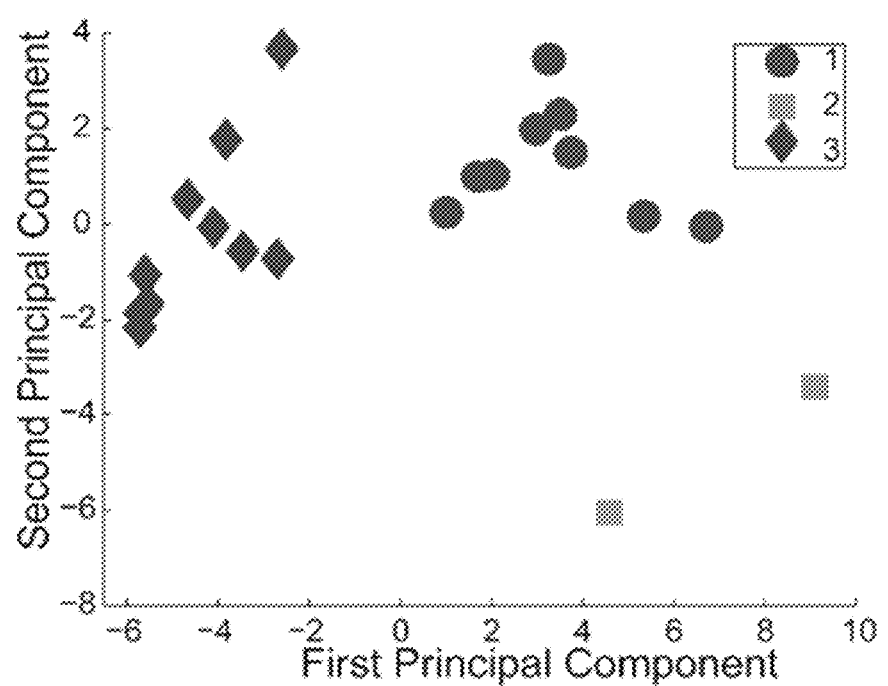

Notably, the found clusters were broadly distributed across the physicochemical space of the tested antibiotics (FIG. 5C). This further supports the conjecture that biology, not chemistry governs compound permeation into cells. The distribution of antibiotics from each cluster appeared to follow its own pattern and converge into the same quadrant of the property plot, which is occupied by relatively hydrophobic compounds with MW below 600 Da. However, branching of clusters into divergent physical spaces is driven by biological determinants such as requirement of specific porins in the OM (Group 1), targeting the OM (Group 3) or specific recognition by efflux pumps (Group 2) (FIG. 5B).

Discussion

In the present work we analyzed contributions of the OM permeability and active efflux in the intracellular accumulation and antibacterial activities in four divergent bacterial species. We found that Pae, Abau, Bt and Bc differ significantly from each other in specificities and capacities of their active efflux pumps and how these pumps interact with the OM barriers. As seen from the increased accumulation of fluorescent probes (FIGS. 2A-3D), hyperporination of the OM was successful in all four species and increased by several folds the flux of compounds across the OM. The kinetic studies of intracellular accumulation of fluorescent probes showed that hyperporination and active efflux act on permeation of compounds independently from each other but in a species-specific manner. Further analyses demonstrated the lack of interdependence between permeability barriers in antibacterial activities as well.

First, in agreement with intracellular accumulation experiments, the effects of efflux and OM on antibacterial activities cluster separately, indicating that these two barriers affect antibiotics independently from each other, and hence, are mechanistically unrelated (FIG. 5A). Second, all antibiotics are affected by permeability barriers and form four distinct clusters (FIG. 5B), suggesting that despite an apparent dominance of biological determinants, antibiotics within the clusters share structural features that are recognized by different barriers. Finally, antibiotics from the same clusters relate to each other through their interactions with permeability barriers and occupy broad but distinct physicochemical spaces (FIG. 5C). The existing heuristics emphasize the size and polarity of compounds as major determinants of permeation across the OM and propensity to be recognized by efflux pumps. In general, very polar and low MW compounds and zwitterionic and high MW compounds are thought to avoid efflux, whereas hydrophobicity of compounds positively correlates with efflux ratios. The four clusters of antibiotics identified here do not conform to these rules (FIG. 5C). It should be recognized that despite chemical diversity and apparent lack of chemical similarity between antibiotics within clusters, the biological recognition is based on similar properties, i.e. substrates share certain properties if they are recognized by the same efflux pump. Hence, antibiotics within the same cluster are governed by the same rules of permeation.

Figure 1C:
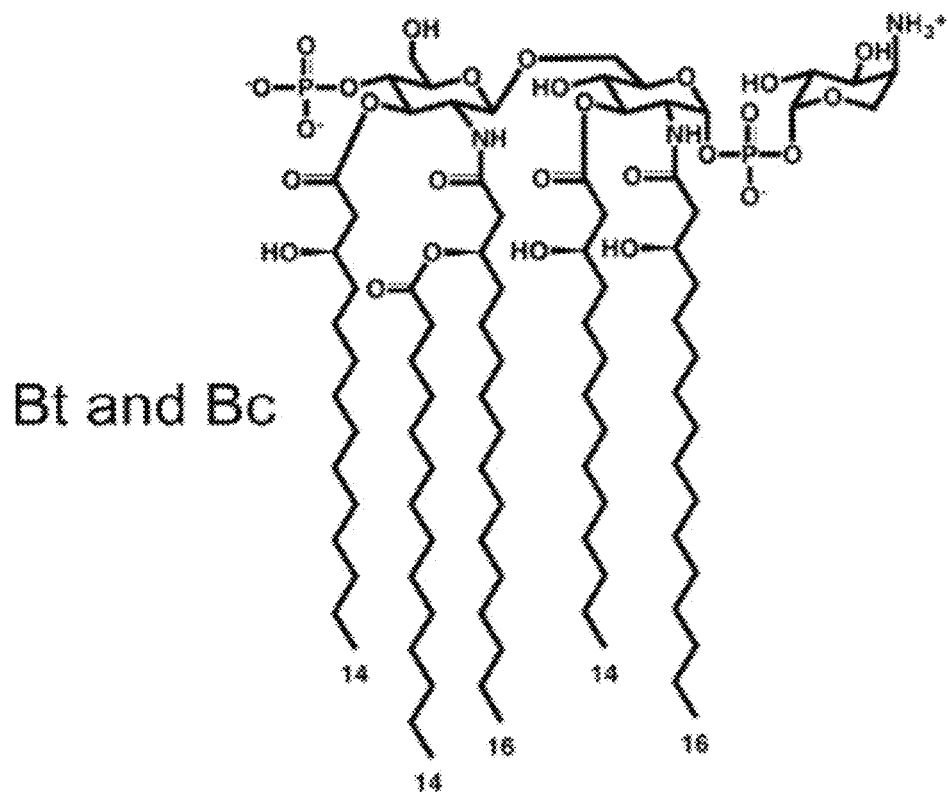
FIG. 1C shows structures of lipid A moieties and hyperporination of the outer membrane of *B. thailandensis* and *B. cepacia* mutants constructed in accordance with the present disclosure. The immunoblotting analyses with a monoclonal anti-His antibody, the copy number of the expressed hyperpores per cell, and MICs of vancomycin (VAN) in the induced cells are shown.
Figure 1C:
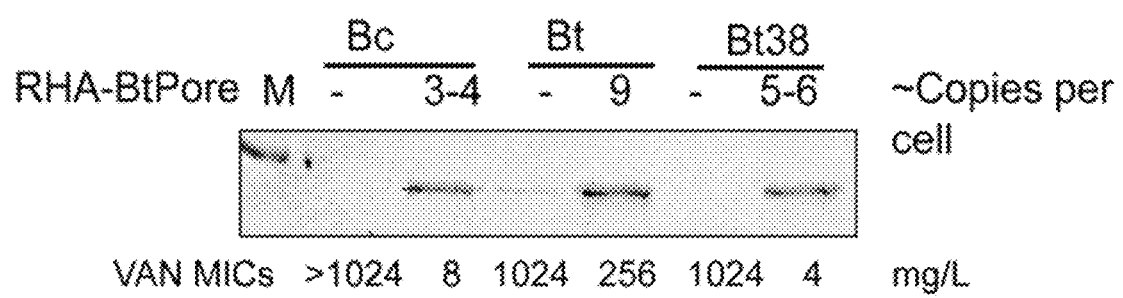

The mechanistic separation between efflux and OM effects is apparent despite significant interspecies differences in the structures of OMs and specificities of efflux pumps. The overall structural organization of all Gram-negative OMs is thought to be similar and comprises an asymmetric bilayer of LPS-phospholipids with general and specific porins and channels embedded into it. Undoubtedly, structural features and variability of both lipids and proteins of OMs contribute to antibiotic permeation. The Pae lipid A is structurally the closest to that of E. coli (FIGS. 1A-1C) and contains the 10-12 carbon long acyl chains that create a hydrophobic layer of 18 Å thick. The OM of Pae, however, does not contain large non-specific porins such as OmpF of E. coli, the factor limiting significantly the uptake of hydrophilic antibiotics (TABLE 7). Consistent with the lack of general porins, with a few exceptions, hyperporination significantly potentiated antibacterial activities in Pae (FIGS. 5A and 7A-7D). Lipid A of Abau is hexa- and hepta-acylated with fatty acids of 12 and 14 carbons in length. As a result, the hydrophobic core of Abau is expected to be thicker, ~23 Å, and lipid A to occupy a larger area per lipid (FIGS. 1A-1C). These features are likely to make the OM of Abau more hydrophobic and are responsible for the modest effect of Abau hyperporination for most of antibiotics and hyper-susceptibility of this species to such amphiphilic antibiotics as macrolides, novobiocin and tetracycline, the antibiotics to which other Gram-negative species are resistant (Tables 7-9). Burkholderia spp. contain tetra- and penta-acylated lipid A with the longest acyl chains of 14 and 16 carbons and an expected thickness of ~24-25 Å. Structures of lipid A in Bc and Bt are very similar and contain a characteristic 4-amino-4-deoxy-L-arabinose (Ara4N) substitution linked to one or both phosphate groups in the lipid A backbone and in the core region of LPS (FIGS. 1A-1C). In other Gram-negative species, Ara4N modifications are present during infections as a protection against antimicrobial peptides. We found that in addition to other antibiotics, these modifications enable the synergism with active efflux against aminoglycosides and polymyxin, antibiotics that are otherwise privileged in their permeation across Gram-negative cell envelopes (Table 8). These structurally diverse OMs present a wide diversity of possible interactions. Yet the molecular determinants of antibiotic interactions with OM are specific and different from those of efflux pumps.

RND pumps are the major contributors to intrinsic and clinical antibiotic resistance in Gram-negative bacteria and are effective against a broad range of structurally unrelated compounds. We unexpectedly found that the functions of RND pumps universally affect activities of all tested antibiotics, even those previously considered to be outside of the efflux recognition space. The effect of efflux on large antibiotics could not be assessed before, because such antibiotics as zeocin, bacitracin or vancomycin penetrate the OM too slowly and do not accumulate significantly in cells. However, hyperporination enabled penetration of these large antibiotics into periplasm and their active efflux. These results demonstrate that the chemical space affected by active efflux is much broader than previously thought and that the size of a compound is not a predictive characteristic of an efflux substrate. This result has further implications for the mechanism of efflux pumps, as the substrate binding sites and tunnels of transporters must be able to accommodate significantly larger than previously thought substrates.

There are also significant species-specific efflux effects. The efflux contribution in Abau is largely defined by the activity of AdeIJK, the major constitutively expressed efflux pump of this species. Although the strains used in this study are susceptible to most of the antibiotics, Abau is notorious for rapid development of multidrug resistance in clinical settings. Overproduction of AdeABC efflux system is observed with a high incidence in multidrug-resistant Abau isolates and results in increased resistance to several antibiotics of choice for the treatment of infections caused by this nosocomial pathogen. Our results predict that the overexpression of these pumps must be very efficient, in order to compensate for the "leaky" OM of Abau and provide antibiotic resistance. MexAB-OprM is the major efflux pump of Pae with broad substrate specificity and likely to be responsible for the observed efflux effects (Table 7). MexCD-OprJ and MexXY-OprM also lacking in PΔ3 strain, are commonly overproduced in clinical isolates. While inactivation of efflux made Pae hypersusceptible to various antibiotics, the OM of PΔ3 became less permeable to fluorescent probes, as seen from the reduced initial rates of HT uptake (FIG. 2B). Thus, Pae cells compensate for the loss of efflux pumps by further reducing the permeability of the OM.

Bc and Bt differ dramatically from each other and other species in their efflux capacities. Our results further suggest that even the limited, 3-4 pores per cell (FIGS. 1A-1C), hyperporination of Bc-RHA-BtPore increases the influx of antibiotics, enough to overwhelm the Bc efflux pumps. As a result, these cells are hypersusceptible to all tested antibiotics. In contrast, the influx remains very slow in the hyperporinated Bt-RHA-BtPore cells, because of highly effective efflux. Indeed, hyperporination had a dramatic effect in BtΔ2-RHA-BtPore cells lacking efflux pumps (Table 8), splitting the two hyperporinated Bt strains into two distant clusters (FIG. 5A). In Bt cells, efflux inactivation alone was responsible for potentiation of antibacterial activities of antibiotics in all four clusters, suggesting that efflux pumps are the dominant contributors to the permeability barrier of this species. Like Pae, *Burkholderia* spp. contain a large array, 10 to 16 operons depending on species, of RND efflux pumps. Among these pumps, only three are characterized in detail in Bt and none in Bc but several transporters are known to function in *B. cenocepacia*. AmrAB-OprA of Bt is related to MexXY-OprM of Pae and contributes to resistance to macrolides and aminoglycosides. BpeAB-OprB is a broad specificity pump responsible for intrinsic antibiotic resistance. Only in Bt cells, inactivation of efflux potentiated activities of aminoglycosides by up to 128-fold independently in the presence or absence of the pore. In contrast, the synergism between inactivation of efflux and hyperporination in BtΔ2-RHA-BtPore was strong in activities of all other antibiotics including polymyxin B. These results suggest that the OM of efflux-deficient Bt cells is susceptible to the action of polycationic antibiotics such as aminoglycosides and polymyxin B. Hence, the Bt efflux pumps are needed to maintain the proper structure of the OM and their inactivation could lead to modifications of LPS. As a result of these structural changes in OM, BtΔ2-RHA-BtPore cells became even more susceptible to antibiotics than analogous Pae and Abau strains. Thus, dramatic differences in the intrinsic levels of antibiotic resistance among the species could be attributed almost entirely to the differences in permeability barriers of their cell envelopes.

It will be understood from the foregoing description that various modifications and changes may be made in the various embodiments of the present disclosure without departing from their true spirit. The description provided herein is intended for purposes of illustration only and is not intended to be construed in a limiting sense. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments of the present disclosure only and are presented in the cause of providing what is believed to be a useful and readily understood description of procedures as well as of the principles and conceptual aspects of the inventive concepts. Changes may be made in the formulation of the various components and compositions described herein, the methods described herein or in the steps or the sequence of steps of the methods described herein without departing from the spirit and scope of the present disclosure.

All patents, published patent applications, and non-patent publications referenced in any portion of this application are herein expressly incorporated by reference in their entirety to the same extent as if each individual patent or publication was specifically and individually indicated to be incorporated by reference.

What is claimed is:

1. A pore-modified mutant of a Gram-negative bacterium, the pore-modified mutant comprising an outer membrane comprising at least one modified OrbA nanopore absent an N-terminal plug domain and absent four external loops, wherein the outer membrane has an enhanced permeability to an antibiotic which is greater than an outer membrane permeability to said antibiotic in a strain of the Gram-negative bacterium comprising a wild-type OrbA nanopore.

2. The pore-modified mutant of claim 1, comprising a wild-type repertoire of efflux pumps wherein active efflux in the pore-modified mutant is not compromised.

3. The pore-modified mutant of claim 1, comprising at least one efflux-deficient efflux pump which causes active efflux in the pore-modified mutant to be compromised.

4. The pore-modified mutant of claim 1, wherein the modified OrbA nanopore has an amino acid sequence selected from the group consisting of SEQ ID NO:2, SEQ ID NO:3, and amino acid sequences having at least 90% identity to SEQ ID NO:3.

5. The pore-modified mutant of claim 1, further comprising a mutation in at least one of the following genes: acrB, acrD, acrEF, emrB, emrY, entS, macB, mdtC, mdtF, tolC, mdfA, emrE, norM, mexAB-oprM, mexCD-oprJ, mexEF-oprN, mexXY, mexGHI, triABC, opmH, mexJKL, adeAB, adeFGH, adeIJK, amrRAB-oprA, bpeAB-oprB, bpeEF-oprC, ompF, ompC, oprD, ompA, carO, oprD, opcP1, and opcP2.

6. The pore-modified mutant of claim 1, wherein the enhanced permeability to an antibiotic is at least ten-fold greater than the outer membrane permeability to said antibiotic in the strain of the Grain-negative bacterium comprising the wild type OrbA nanopore.

7. The pore-modified mutant of claim 6, wherein the antibiotic is selected from the group consisting of Amikacin, Bacitracin, Gentamicin, Streptomycin, Levofloxacin, Nalidixic acid, Lincomycin, Chloramphenicol, Triclosan, Tetracycline, Ciprofloxacin, Proflavine, Ciprofloxacin, Cloxacillin, Carbenicillin, Ampicillin, Coumermycin, Kanamycin, Rifampin, Vancomycin, Doxycycline, Polymyxin B, Erythromycin, Azithromycin, Virginiamycin, Novobiocin, Tobramycin, Meropenem, and Zeocin.

8. Thu pore-modified mutant of claim 1, comprising an increased sensitivity to at least one compound of the group consisting of Amikacin, Bacitracin, Gentamicin, Streptomycin, Levofloxacin, Nalidixic acid, Lincomycin, Chloramphenicol, Triclosan, Tetracycline, Ciprofloxacin, Proflavine, Ciprofloxacin, Cloxacillin, Carbenicillin, Ampicillin, Coumermycin, Kanamycin, Rifampin, Vancomycin, Doxycycline, Polymyxin B, Erythromycin, Azithromycin, Virginiamycin, Novobiocin, Tobramycin, Meropenem, and Zeocin, as compared to a wild-type version of the Gram-negative bacterium.

9. The pore-modified mutant of claim 8, wherein the increased sensitivity is measured as a decrease in minimum inhibitory concentration in a range of at least 10-fold to at least 1000-fold.

10. A pore-modified mutant of a Gram-negative bacterium, the pore-modified mutant having an outer membrane comprising at least one modified OrbA nanopore absent an N-terminal plug domain and absent four external loops, wherein the outer membrane has an enhanced permeability to an antibiotic which is greater than an outer membrane permeability to said antibiotic in a strain of the Gram-negative bacterium comprising a wild-type OrbA nanopore; and the outer membrane further comprising either (1) a wild-type repertoire of efflux pumps wherein active efflux in the pore-modified mutant is not compromised, or (2) at least one efflux-deficient efflux pump which causes active efflux in the pore-modified mutant to be compromised.

* * * * *

UNITED STATES PATENT AND TRADEMARK OFFICE
CERTIFICATE OF CORRECTION

PATENT NO.         : 11,021,521 B2
APPLICATION NO.    : 16/134696
DATED              : June 1, 2021
INVENTOR(S)        : Helen Zgurskaya and Jon Weeks Page 1 of 1

It is certified that error appears in the above-identified patent and that said Letters Patent is hereby corrected as shown below:

In the Claims

Column 55, Claim 8, Line 8, delete "Thu" and insert --The-- therefor.

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*